United States Patent
Foster et al.

(10) Patent No.: US 11,400,057 B2
(45) Date of Patent: Aug. 2, 2022

(54) TREATMENT OF VULVAR PAIN

(71) Applicant: University of Rochester, Rochester, NY (US)

(72) Inventors: David Foster, Rochester, NY (US); Megan L. Falsetta Wood, Rochester, NY (US); Richard P. Phipps, Rochester, NY (US)

(73) Assignee: University of Rochester, Rochester, NY (US)

( * ) Notice: Subject to any disclaimer, the term of this patent is extended or adjusted under 35 U.S.C. 154(b) by 247 days.

(21) Appl. No.: 16/590,973

(22) Filed: Oct. 2, 2019

(65) Prior Publication Data
US 2020/0121617 A1 Apr. 23, 2020

Related U.S. Application Data

(60) Provisional application No. 62/747,901, filed on Oct. 19, 2018.

(51) Int. Cl.
*A61K 31/121* (2006.01)
*A61P 15/02* (2006.01)
*A61K 9/00* (2006.01)

(52) U.S. Cl.
CPC .......... *A61K 31/121* (2013.01); *A61K 9/0014* (2013.01); *A61P 15/02* (2018.01)

(58) Field of Classification Search
CPC ............................ A61K 9/0014; A61P 15/02
See application file for complete search history.

(56) References Cited

U.S. PATENT DOCUMENTS

| 5,912,006 A | 6/1999 | Bockow et al. |
| 2014/0079631 A1* | 3/2014 | Serhan ................ A61P 11/00 424/1.65 |
| 2018/0110751 A1 | 4/2018 | Sciavolino et al. |
| 2018/0200375 A1 | 7/2018 | Sciavolino et al. |

FOREIGN PATENT DOCUMENTS

| WO | 2013170006 A2 | 11/2013 |
| WO | 2017210604 A1 | 12/2017 |

OTHER PUBLICATIONS

Sobel et al., Female Sexual Pain Disorders, Mar. 6, 2009, p. 95-104 (Year: 2009).*
Wesselmann et al., Pain, 2014;155(9):1696-1701 (Year: 2014).*
Falsetta, M. et al., "A Much-Needed Model for the Preclinical Testing of New Vulvodynia Theripies"; Journal of Lower Genital Tract Disease (2017); vol. 21:4; Supplemental 1; 2 pgs.
Dmitrieva, N. et al., "Resolvins RvD1 and 17(R)-RvD1 Alleviate Signs of Inflammation in a Rat Model Endometriosis"; Fertility and Sterility (2014); vol. 102:4; pp. 1191-1196.
Murina, F., "Alpha Lipoic Acid Plus Omega-3 Fatty Acids for Vestibulodynia Associates with Painful Bladder Syndrome"; J. Obster Gynaecol Can (2017); vol. 39:3; pp. 131-137.
(Continued)

*Primary Examiner* — San Ming R Hui
(74) *Attorney, Agent, or Firm* — Fox Rothschild LLP

(57) ABSTRACT

The present invention relates to methods of treating female reproductive tract irritation (such as pain and pruritus) or/and inflammation.

15 Claims, 10 Drawing Sheets

(56) References Cited

OTHER PUBLICATIONS

Serhan, C. N. et al., "The Resolution Code of Acute Inflammation: Novel Pro-Resolving Lipid Mediators in Resolutions"; Seminars in Immunology (2015); vol. 27:3; pp. 200-215.
Falsetta, M. L. et al., "A Review of the Available Clinical Therapies for Vulvodynia Management and New Data Implicating Pro-Inflammatory Mediators in Pain Elicitation"; BJOG (2017); vol. 124:2; pp. 210-218.
Mysrayn, Y. F. A. et al., "Anti-Inflammatory Activity of Babassu Oil and Development of a Microemulsion System for Topical Delivery"; Evidence-Based Complementary and Alternative Medicine (2017); vol. 2017; 14 pgs.
Falsetta, M. L. et al., "Specialized Pro-Resolving Mediators: A Promising New Therapeutic Avenue for Vulvodynia"; Journal of Lower Genital Tract Disease (2019); vol. 23:4, Supplemental 1.
Ramsden, C. E. et al., Dietary linoleic acid-induced alterations in pro- and anti-nociceptive lipid autacoids: Implications for idiopathic pain syndromes?; Molecular Pain (2016); vol. 12; 14 pgs.
Hesselink, J. et al., "New Topical Treatment of Vulvodynia Based on the Pathogenetic Role of Cross Talk Between Nociceptors, Immunocompetent Cells, and Epithelial Cells"; Journal of Pain Research (2016); vol. 9; pp. 757-762.
Lev-Sagie, A. et al., "Recent Advances in Understanding Provoked Vestibulodynia"; F1OOO Research (2016); 10 pgs.
Serhan, C. N., "Novel Pro-Resolving Lipid Mediators in Inflammation are Leads for Resolution Physiology"; Nature (2014); vol. 510:7503; pp. 92-101.
Falsetta, M. L. et al., "Identification of Novel Mechanisms Involved in Generating Localized Vulvodynia Pain"; Am. J. Obstet Gynecol (2015); vol. 213:1; 27 pgs.
Foster, D.C., "Site-Specific Mesenchymal Control of Inflammatory Pain to Yeast Challenge in Vulvodynia Afflicted and Pain-Free Women"; Pain (2015); vol. 156:3; pp. 386-396.

\* cited by examiner

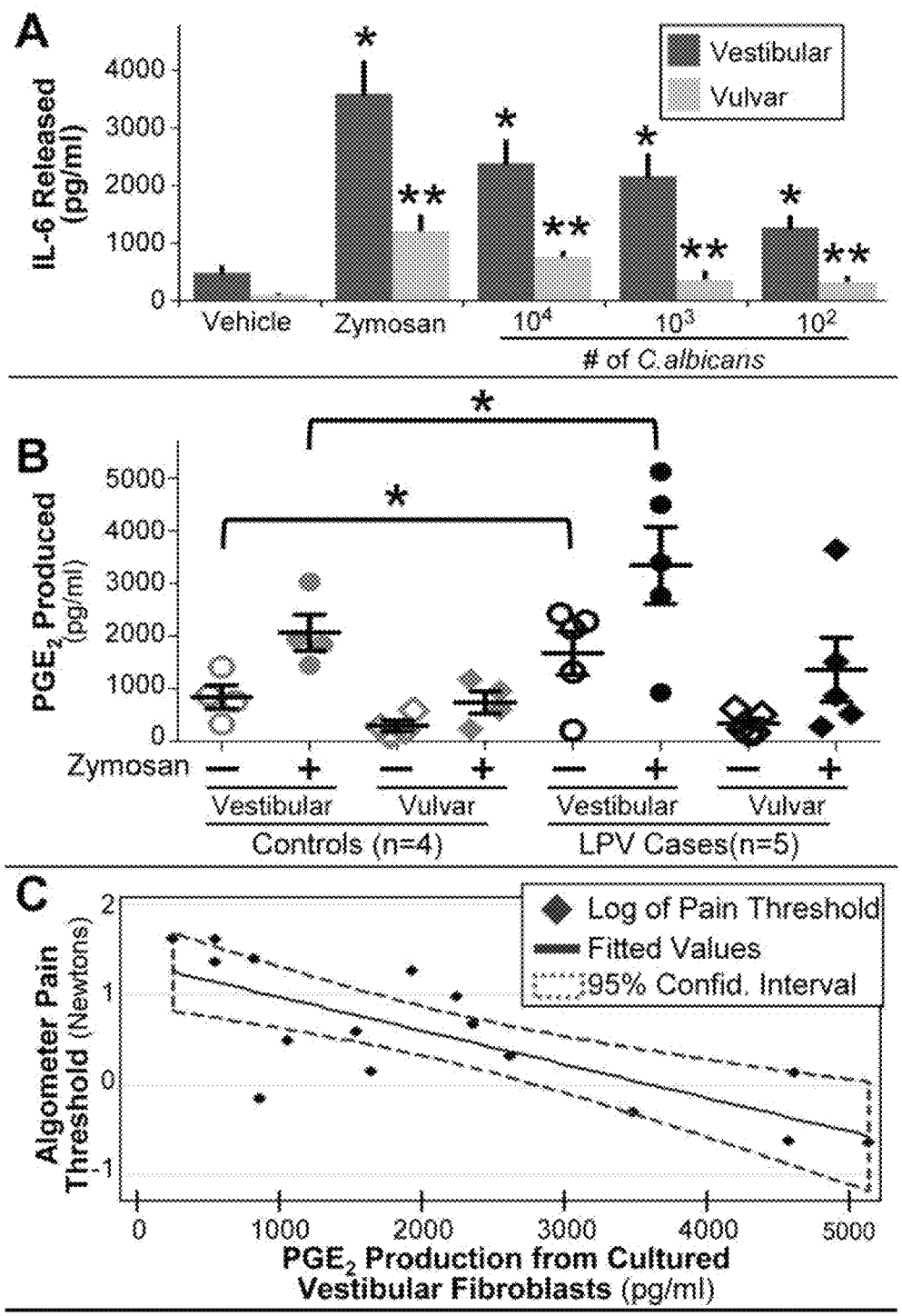
FIGs. 3A, 3B, and 3C

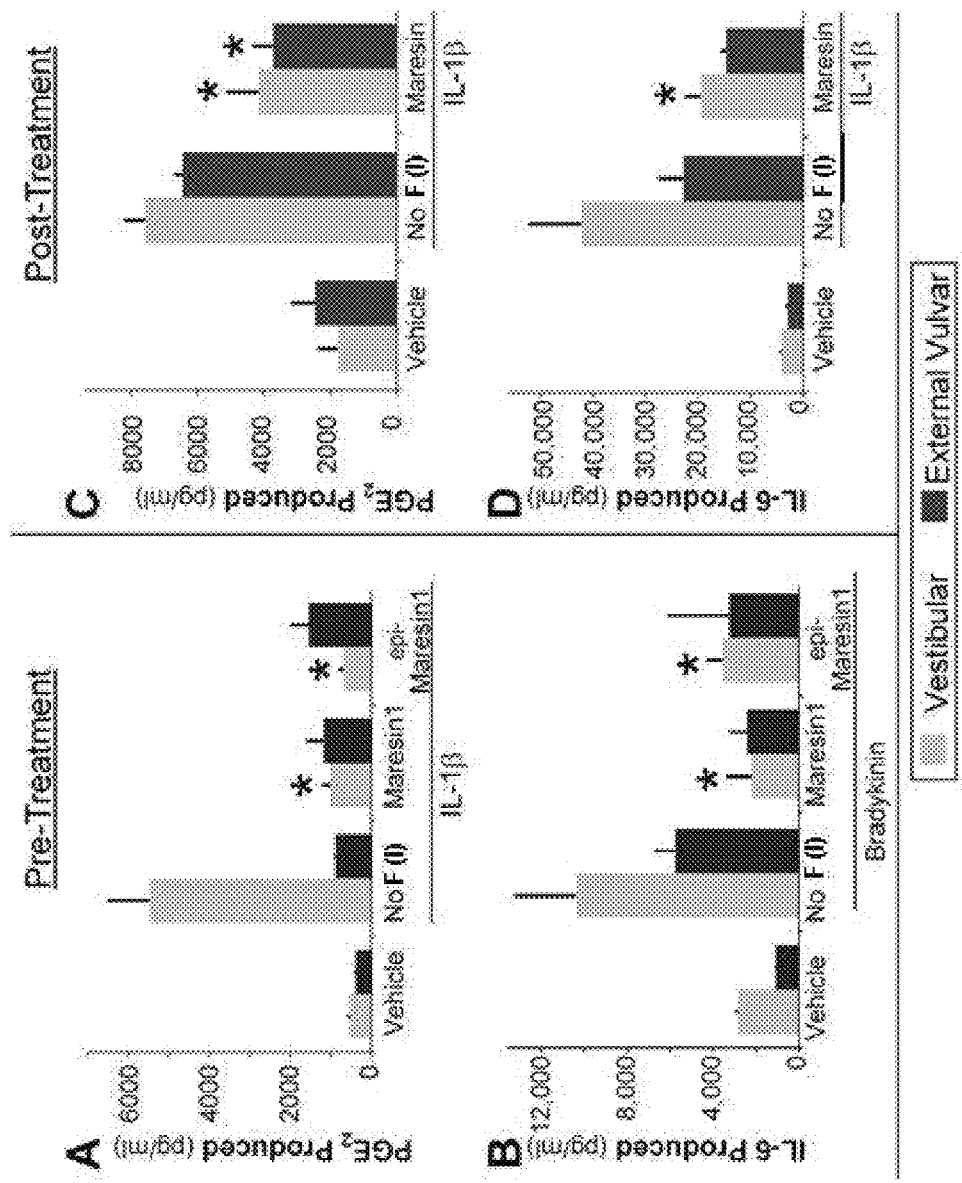
FIGS. 4A, 4B, 4C, and 4D

FIGS. 6A, 6B, and 6C

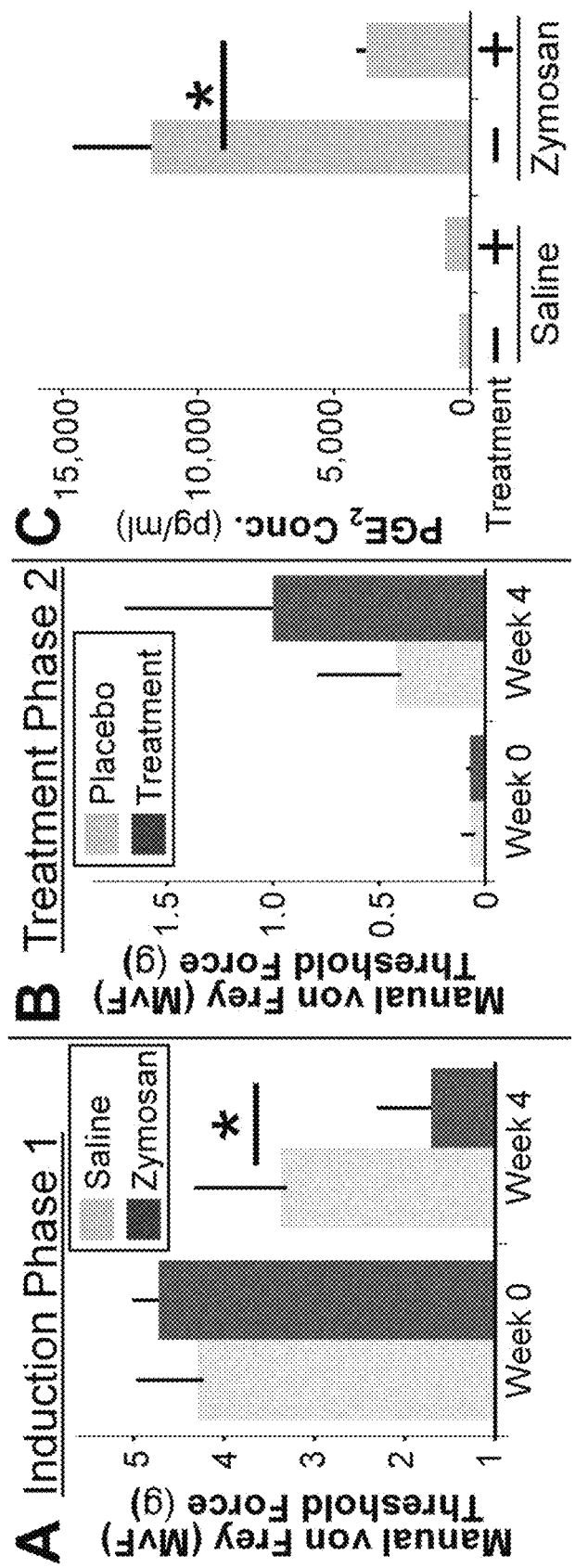
FIGs. 10A, 10B, and 10C

TREATMENT OF VULVAR PAIN

GOVERNMENT INTERESTS

This invention was made with government support under HD069313 awarded by National Institutes of Health. The government has certain rights in the invention.

FIELD OF THE INVENTION

This invention relates to treating female reproductive tract irritation or/and inflammation.

BACKGROUND OF THE INVENTION

Irritation, such as pain and pruritus, from the female reproductive tract is a significant clinical problem for which there are few effective therapies.

Vulvar pain or persistent vulvar pain can be caused by specific disorders such as infectious (e.g. recurrent candidiasis, herpes, trichomoniasis, etc.); inflammatory (e.g. lichen sclerosus, lichen planus, immunobullous disorders, etc.); neoplastic (e.g. Paget disease, squamous cell carcinoma, etc.); neurologic (e.g. post-herpetic neuralgia, nerve compression or injure, neuroma, etc.); trauma (e.g. female genital cutting, obstetrical, etc.); Iatrogenic (e.g. post-operative, chemotherapy, radiation, etc.); hormonal deficiencies (e.g. genito-urinary syndrome of menopause, vulvo-vaginal atrophy, lactational amenorrhea, etc.).

In addition, vulvar pain can be idiopathic which is classified as vulvodynia.[1,2] Vulvodynia is a vulvar chronic pain of at least 3 months of duration, without clear identifiable cause, and may have potential associated factors. Vulvodynia affects[8] the vulva, the external female genital organs. This includes the labia, clitoris, and vaginal opening. Pain is the most notable symptom of vulvodynia, and can be characterized as a burning, stinging, irritation or sharp pain that occurs in the vulva and entrance to the vagina. This pain may be generalized and/or localized (vestibulodynia, clitorodynia, hemivulvodynia), constant, intermittent or provoked (happen only when the vulva is touched). The most common subset of vulvodynia is localized provoked vulvodynia (LPV) which is characterized by acute and lasting pain in response to light touching of the vulvar vestibule (area immediately surrounding the vaginal opening), afflicts as many as 1 in 3 women within their lifetime and causes significant psychological distress and sexual dysfunction (Harlow, B L; Kunitz, C G; Nguyen, R H; Rydell, S A; Turner, R M; MacLehose, R F. Am J Obstet Gynecol 2014, vol. 210, pp. 40 e1-8). Therefore, LPV is a significant women's health issue.

In the most severe cases, women may have both a pain cause by a specific disorder and vulvodynia.

Treatment of irritation, such as vulvar pain and pruritus, may involve a number of different measures.[9] However, all currently available therapies only manage pain and psychological distress, but none is universally effective to date and the evidence to support their effectiveness is often poor.

It is really remarkable that current treatments have not addressed the underlying biological causes of disease and, therefore, an approach in this regard could improve even restore the patient's quality of life.

The compounds mentioned in the present invention have been disclosed in WO2010033509 and WO2013170006 for the treatment of different inflammatory diseases but not specifically for the treatment of female reproductive tract irritation.

SUMMARY OF INVENTION

This invention relates to treating female reproductive tract irritation, such as pain and pruritus, or/and inflammation.

Accordingly, in one aspect, the invention provides a method of reducing, preventing, or treating lower genital tract irritation in a subject comprising administering to a subject in need an effective amount of at least one compound having the Formula (I):

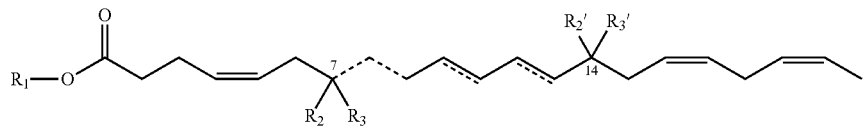

wherein 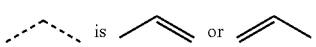 is a double bond with the Z or E configuration;

wherein

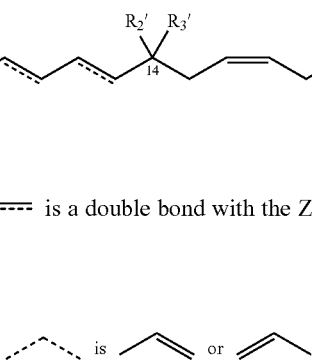

with the Z or E configuration;

wherein the carbon at C7 and C14 are, independently, either R or S;

wherein $R_1$, is selected from hydrogen, (C1-C6) alkyl, glyceryl, (C3-C8) cycloalkyl, cyclohexyl, (C4-C11) cycloalkylalkyl, (C5-C15) aryl, (C6-C16) arylalkyl, 2-6 membered heteroalkyl, 3-8 membered cycloheteroalkyl, 4-11 membered cycloheteroalkylalkyl, (C5-C14) heteroaryl and 6-21 membered heteroarylalkyl;

wherein each of $R_2$ and $R_{2'}$ is independently a hydroxyl group or a hydrogen atom, with the proviso that at least one of $R_2$ and $R_{2'}$ is a hydroxyl group;

wherein $R_3$, if present, is selected from hydrogen, (C1-C6) alkyl, (C3-C8) cycloalkyl, cyclohexyl, (C4-C11) cycloalkylalkyl, (C5-C15) aryl, (C6-C16) arylalkyl, and 2-6 membered heteroalkyl;

wherein $R_{3'}$ is selected from hydrogen, (C1-C6) alkyl, (C3-C8) cycloalkyl, (C4-C11) cycloalkylalkyl, (C5-C15) aryl, (C6-C16) arylalkyl, and 2-6 membered heteroalkyl;

or a pharmaceutically acceptable salt thereof; and optionally, a pharmaceutically acceptable carrier;

In one embodiment, compounds of Formula (I) are in the triglyceride, diglyceride, and/or monoglyceride form.

In one embodiment, the lower genital tract irritation is genital tract pain.

In a particular embodiment, the genital tract pain is idiopathic.

In a more particular embodiment, the idiopathic lower genital tract pain is vulvodynia.

Even more particularly, the vulvodynia is localized provoked vulvodynia (LPV).

In a preferred embodiment, compounds of Formula (I) are Maresin-1, 7S-Maresin-1, 14-methyl-Maresin 1, 7-methyl-Maresin 1, 7,14-dimethyl-Maresin 1, and 14-hydroxy-docosahexaenoic acid (14-HDHA) and the corresponding acceptable pharmaceutical salt or esters thereof.

The method can further comprise administering at least one compound of Formula (I) with one or more therapeutic agents (e.g., one or more specialized pro-resolving mediators (SPMs), one or more SPM precursors, an anti-microbial agent and/or an antiviral agent) to the subject.

The details of one or more embodiments of the invention are set forth in the description below. Other features, objectives, and advantages of the invention will be apparent from the description and from the claims.

BRIEF DESCRIPTION OF THE DRAWINGS

FIGS. 3A, 3B and 3C are a set of diagrams showing that inflammatory mediator production is elevated in vestibular cells from LPV patients compared to vulvar cells or control subjects. Panel A: IL-6 released in response to decreasing doses of live $C.$ $albicans$. *$p<0.05$ vehicle vs. dose of $C.$ $albicans$ (for vestibular cells only), **$p<0.05$ vestibular vs. vulvar cells for a particular dose. ANOVA, n=4. Vestibular cells show a strong response, while vulvar cells show no significant response to a dose up to 1000 times greater.[3] Panel B: Cultured fibroblasts were stimulated with vehicle or Zymosan (100 μg/ml) for 24 hours, then media were analyzed for $PGE_2$.[10,12] Zymosan induced a significant increase in $PGE_2$ over corresponding vehicle treatment. Vestibular fibroblasts from LPV case patients produced more $PGE_2$ compared to vestibular fibroblasts from control subjects. Mean+/−SEM. ANOVA *$p<0.05$. Panel C: Scatter plot of fibroblast $PGE_2$ production plotted against log transformation of mucocutaneous pain threshold, performed before tissue sampling, from identical anatomical sites. Central line (solid red) represents fitted values of linear regression delimited by 95% confidence intervals (blue dotted line). t=2.58, p=0.04.

FIGS. 4A, 4B, 4C, and 4D are a set of diagrams showing that $PGE_2$ and IL-6 production is reduced by compounds of Formula (I). Patient vestibular or vulvar fibroblasts were pre-treated for 10 hours with Maresin land epi-Maresin 1 at a 5 nM concentration, then activated with IL-1β (Panel A; 10 pg/ml) or bradykinin (Panel B; 100 nM) for 48 hr. Culture media were collected and analyzed for $PGE_2$ (Panel A) or IL-6 (Panel B) content. Patient fibroblasts were also activated first with IL-1β for 30 min then treated with 5 nM Maresin 1 for 18 hours, followed by a booster dose for 6 hr. Culture media were collected and analyzed for $PGE_2$ (Panel C) or IL-6 (Panel D) content. Mean+/−SEM of n=3, ANOVA *$p<0.05$ vs. activation only (no compounds of Formula (I) (F (I))). These results were consistent for several additional LPV patient strains.

FIGS. 10A, 10B and 10C are a set of diagrams showing manual von Frey assessment of pain threshold that denotes improvement in threshold with treatment. Decreased thresholds in Zymosan-treated mice after 4 weeks of injection reflects increased pain/sensitivity, Mean+/−SEM, n=8 saline, n=12 Zymosan, ANOVA *$p<0.05$ (Panel A). Therapeutic treatment after the induction phase increased pain thresholds. Mean+/−SEM, n=7, p>0.05 (Panel B). Vulvovaginal lavage fluid was analyzed for PGE2 content (Panel C). Mice receiving Zymosan had elevated PGE2 in their lavage fluid versus mice receiving saline injection. Furthermore, treated mice with allodynia had reduced PGE2. Mean+/−SEM, n=7, ANOVA *$p<0.05$.

In the figures, F (I) means compounds of Formula (I).

DETAILED DESCRIPTION OF THE INVENTION

This invention is based, at least in part, on unexpected discoveries that fibroblasts isolated and cultured from sites of pain in LPV patients produce very high levels of pro-inflammatory and pro-pain mediators compared to "pain free" sites.

Figure 1:
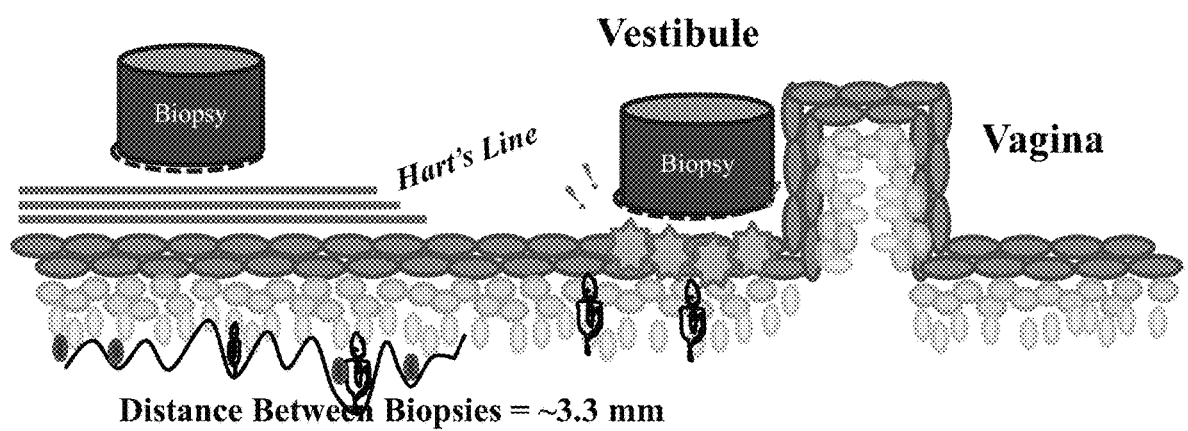
FIG. 1 is a diagram showing the sites of intense pain at the vestibule of LPV patients are in close proximity to non-painful sites of the external vulva and related biopsy sites.
Figures 2A, 2B:
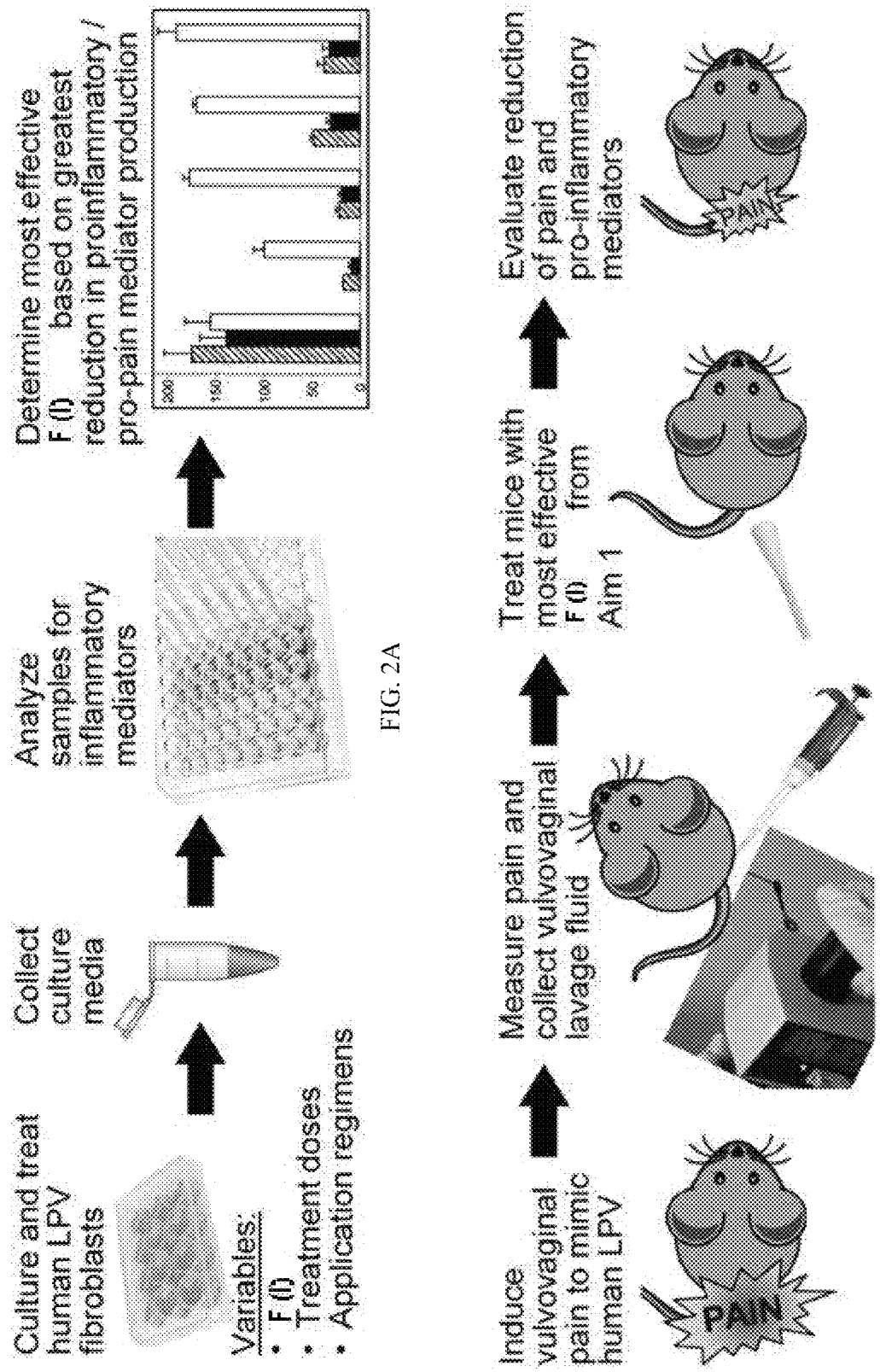
FIGS. 2A and 2B are a set of diagrams showing procedures for (A) investigating the ability to reduce pro-inflammatory and pro-pain mediator production form primary human cells in an in vitro LPV model and (B) evaluating the efficacy of compounds in alleviating pain using a preclinical mouse model of LPV.[11]

As disclosed herein, it was discovered that the vulvar vestibule expresses a unique inflammatory profile involving the elevated production of pro-pain and pro-inflammatory mediators, e.g., prostaglandin $E_2$ ($PGE_2$) and interleukin-6 (IL-6) by fibroblast strains isolated from the vestibule site (FIG. 1, "Vestibule"). Furthermore, elevated pro-inflammatory mediator release correlates with pain profiles in women. Therefore, effective therapeutics for vulvodynia would ideally reduce pro-inflammatory signaling, while preserving the natural ability of these cells to respond to harmful proinflammatory stimuli. The investigation described herein has identified mechanisms by which hypersensitivity to certain inflammatory stimuli leads to heightened pain. Specifically, it was demonstrated that pain in LPV patients is directly correlated with the production of pro-inflammatory and pro-pain mediators from fibroblasts cultured from biopsies of painful sites (FIG. 1, "Vestibule").

As described herein, fibroblasts producing high levels of pro-pain and pro-inflammatory mediators can be isolated from patients at sites with intense, quantifiable pain. As they abundantly produce pro-pain mediators and maintain their relevant phenotypes in culture, the primary vestibular fibroblasts are valuable in modeling LPV and were used successfully here to identify new therapeutic agents that can be used to resolve atypical inflammatory mediator production in LPV patients that leads to regional pain.

This invention addresses the treatment of female reproductive tract irritation, such as pain and pruritus. Specifically, this invention provides a treatment of vulvar pain or vulvar persistent pain associated to a specific disorder such as inflammation or/and idiopathic pain, and more particularly to vulvodynia, whose etiology is unclear and where no effective medical therapy has been developed.

In particular, the compounds represented by Formula (I) have resulted to be effective against lower genital tract irritation, such as vulvar pain, and more particularly to vulvodynia, among others.

Accordingly, in one aspect, the invention provides a method of reducing, preventing, or treating lower genital tract irritation in a subject comprising administering to a subject in need an effective amount of at least one compound having the Formula (I):

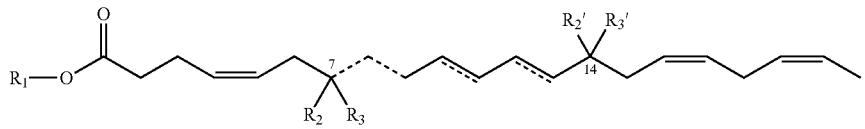

wherein ═══ is a double bond with the Z or E configuration;
wherein

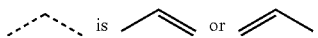

with the Z or E configuration;
wherein the carbon at C7 and C14 are, independently, either R or S;
wherein $R_1$, is selected from hydrogen, (C1-C6) alkyl, glyceryl, (C3-C8) cycloalkyl, cyclohexyl, (C4-C11) cycloalkylalkyl, (C5-C15) aryl, (C6-C16) arylalkyl, 2-6 membered heteroalkyl, 3-8 membered cycloheteroalkyl, 4-11 membered cycloheteroalkylalkyl, (C5-C14) heteroaryl and 6-21 membered heteroarylalkyl;
wherein each of $R_2$ and $R_{2'}$ is independently a hydroxyl group or a hydrogen atom, with the proviso that at least one of $R_2$ and $R_{2'}$ is a hydroxyl group;
wherein $R_3$, if present, is selected from hydrogen, (C1-C6) alkyl, (C3-C8) cycloalkyl, cyclohexyl, (C4-C11) cycloalkylalkyl, (C5-C15) aryl, (C6-C16) arylalkyl, and 2-6 membered heteroalkyl;
wherein $R_{3'}$ is selected from hydrogen, (C1-C6) alkyl, (C3-C8) cycloalkyl, (C4-C11) cycloalkylalkyl, (C5-C15) aryl, (C6-C16) arylalkyl, and 2-6 membered heteroalkyl;

or a pharmaceutically acceptable salt thereof; and
optionally, a pharmaceutically acceptable carrier;
In one embodiment, compounds of Formula (I) are in the triglyceride, diglyceride and/or monoglyceride form.
In other embodiment, $R_1$ is methyl or ethyl.
The compounds of Formula (I) are SPMs or SPM Precursors.
In some embodiments, examples of compounds of Formula (I) include, but are not limited to:
Maresin 1 (MaR1; 7R,14S-dihydroxy-docosa-4Z,8E,10E,12Z,16Z,19Z-hexaenoic acid);
7S-Maresin 1 (7S-MaR1; 7S,14S-dihydroxy-docosa-4Z,8E,10E,12Z,16Z,19Z-hexaenoic acid);
14S-methyl-Maresin 1 (7R,14S-dihydroxy-14-methyl-docosa-4Z,8E,10E,12Z,16Z,19Z-hexaenoic acid);
14R-methyl-Maresin 1 (7R,14R-dihydroxy-14-methyl-docosa-4Z,8E,10E,12Z,16Z,19Z-hexaenoic acid);
14R/S-methyl-Maresin 1 (7R,14R/S-dihydroxy-14-methyl-docosa-4Z,8E,10E,12Z,16Z,19Z-hexaenoic acid);
7R,14S-dihydroxi-7,14-dimethyl-docosa-4Z,8E,10E,12Z,16Z,19Z-hexaenoic acid);
7R-methyl-Maresin 1 (7R,14S-dihydroxy-7-methyl-docosa-4Z,8E,10E,12Z,16Z,19Z-hexaenoic acid);
7S-methyl-Maresin 1 (7S,14S-dihydroxy-7-methyl-docosa-4Z,8E,10E,12Z,16Z,19Z-hexaenoic acid);
7S,14S-diHDHA (7S,14S-dihydroxy-docosa-4Z,8E,10Z,12E,16Z,19Z-hexaenoic acid);
14S-HDHA (14S-hydroxy-docosa-4Z,7Z,10Z,12E,16Z,19Z-hexaenoic acid);
14R-HDHA (14R-hydroxy-docosa-4Z,7Z,10Z,12E,16Z,19Z-hexaenoic acid);
14R-methyl-HDHA (14R-hydroxy-14-methyl-docosa-4Z,7Z,10Z,12E,16Z,19Z-hexaenoic acid);
14S-methyl-HDHA (14S-hydroxy-14-methyl-docosa-4Z,7Z,10Z,12E,16Z,19Z-hexaenoic acid);
or a pharmaceutically acceptable salt or ester thereof.
In other embodiment, the compounds of Formula (I) are selected from:
Maresin 1 (MaR1; 7R,14S-dihydroxy-docosa-4Z,8E,10E,12Z,16Z,19Z-hexaenoic acid);
7S-Maresin 1 (7S-MaR1; 7S,14S-dihydroxy-docosa-4Z,8E,10E,12Z,16Z,19Z-hexaenoic acid);
14S-methyl-Maresin 1 (7R,14S-dihydroxy-14-methyl-docosa-4Z,8E,10E,12Z,16Z,19Z-hexaenoic acid);
14R-methyl-Maresin 1 (7R,14R-dihydroxy-14-methyl-docosa-4Z,8E,10E,12Z,16Z,19Z-hexaenoic acid);
14R/S-methyl-Maresin 1 (7R,14R/S-dihydroxy-14-methyl-docosa-4Z,8E,10E,12Z,16Z,19Z-hexaenoic acid);
7R,14S-dihydroxi-7,14-dimethyl-docosa-4Z,8E,10E,12Z,16Z,19Z-hexaenoic acid);
and a pharmaceutically acceptable salt or ester thereof.
In other preferred embodiment, the compounds of Formula (I) are selected from:
14S-methyl-Maresin 1 (7R,14S-dihydroxy-14-methyl-docosa-4Z,8E,10E,12Z,16Z,19Z-hexaenoic acid);
14R-methyl-Maresin 1 (7R,14R-dihydroxy-14-methyl-docosa-4Z,8E,10E,12Z,16Z,19Z-hexaenoic acid);

14R/S-methyl-Maresin 1 (7R,14R/S-dihydroxy-14-methyl-docosa-4Z,8E,10E,12Z,16Z,19Z-hexaenoic acid);
7R,14S-dihydroxi-7,14-dimethyl-docosa-4Z,8E,10E,12Z,16Z,19Z-hexaenoic acid);
and a pharmaceutically acceptable salt or ester thereof.

In other embodiment, the compounds of Formula (I) are selected from:
14S-HDHA (14S-hydroxy-docosa-4Z,7Z,10Z,12E,16Z,19Z-hexaenoic acid);
14R-HDHA (14R-hydroxy-docosa-4Z,7Z,10Z,12E,16Z,19Z-hexaenoic acid);
14R/S-HDHA (14R/S-hydroxy-docosa-4Z,7Z,10Z,12E,16Z,19Z-hexaenoic acid);
and a pharmaceutically acceptable salt or ester thereof.

In a particular embodiment of the invention, the lower genital tract irritation is lower genital tract pain or pruritus.

In a more particular embodiment, the lower genital tract pain or pruritus is an inflammatory pain or pruritus associated with a genital tract inflammatory condition, such as lichen planus, lichen sclerosus, desquamative inflammatory vaginitis, atrophic vulvovaginitis associated with breast cancer.

In another more particular embodiment, the lower genital tract pain is idiopathic.

In a more particular embodiment, the idiopathic lower genital tract pain is vulvodynia.

Vulvodynia is the most common cause of longstanding dyspareunia (painful sexual intercourse) in premenopausal women, characterized by vulvar pain of at least 3 months duration, without clear identifiable cause, which may have potential associated factors. The most common subtype of vulvodynia is LPV characterized by pain to light touch limited to the vulvar vestibule surrounding the vaginal opening. In women with LPV, chronic vestibular pain is crippling, impacting every aspect of life and exacerbating comorbidities, such as fibromyalgia and painful bladder. The devastating impact of LPV includes sexual dysfunction, infertility, depression, and even suicide.

Therefore, even more particularly, the vulvodynia is localized provoked vulvodynia (LPV).

The compounds of Formula (I) of this invention resolve inflammation and pain without impairing normal host defense. The resolution of inflammation and pain, once thought to be a passive process during which pro-inflammatory signaling tapers off, is now known to be an active process mediated by the compounds of Formula (I). The compounds of Formula (I) actively reduce pro-inflammatory signaling, promote bacterial clearance, reduce pain, and accelerate wound healing. Compounds of Formula (I) are not traditional anti-inflammatory agents and are not immunosuppressive; they do not affect the body's ability to sense and respond to infection or injury.

As disclosed herein, compounds of Formula (I) can be ideal therapeutic agents for vulvodynia, as they foster wound healing, promote bacterial clearance, and reduce pain and pro-inflammatory signaling. Although compounds of Formula (I) have not been clinically tested as in vulvodynia therapy, evidence presented here supports that these compounds are efficacious in reducing pain-provoking pro-inflammatory mediator production and in turn, reduce LPV-associated pain in vivo.

In one embodiment, this invention relates to using compounds of Formula (I) to promote bacterial clearance and reduce pain, and accelerate wound healing. Using an in vitro model described herein, inventors identified compounds of Formula (I) highly effective in reducing IL-6 and $PGE_2$ production in cells when administered prior to inflammatory stimulation. Furthermore, Maresin-1 is highly effective in reducing IL-6 and $PGE_2$ in already activated cells, suggesting this compound is effective throughout the entire disease process. The results described herein suggest that compounds of Formula (I) are effective idiopathic, an inflammatory pain associated with a genital tract inflammatory condition, such as lichen planus, lichen sclerosus, desquamative inflammatory vaginitis, and atrophic vulvovaginitis associated with breast cancer and vulvodynia therapies.

As also disclosed herein, a robust and reproducible mouse model of LPV was developed to assess therapeutic intervention against vulvar pain (the first of its kind). The model couples real-time pro-inflammatory mediator quantification with mechanical pain testing via an electronic von Frey to monitor pain and inflammation over time. Inventors were able to establish stable allodynia in mice, lasting more than several months. During allodynia induction, it was found that pain thresholds decreased, while pro-inflammatory mediator levels (e.g., $PGE_2$) increased within collected vulvovaginal fluids, consistent our in vitro findings. Inventors then treated mice daily with topical Maresin-1, which increased pain thresholds, while suppressing $PGE_2$ levels. The in vitro and in vivo findings disclosed herein suggest that topical application of compounds of Formula (I) can reduce vulvar pain and inflammation and would represent an ideal therapy for vulvodynia.

In one embodiment, one or more compounds of Formula (I) can be formulated with other SPMs and/or SPM precursors not included in Formula (I). Such SPMs and/or SPM precursors are described in WO2013170006.

In a particular embodiment, said other SPMs and/or SPM precursors not included in Formula (I) are selected from:
17S-HDHA (17S-hydroxy-docosa-4Z,7Z,10Z,13Z,15E,19Z-hexaenoic acid);
17R-HDHA (17R-hydroxy-docosa-4Z,7Z,10Z,13Z,15E,19Z-hexaenoic acid);
18 S-HEPE (18S-hydroxy-eicosa-5Z,8Z,11Z,14Z,16E-pentaenoic acid);
18R-HEPE (18R-hydroxy-eicosa-5Z,8Z,11Z,14Z,16E-pentaenoic acid);
or a pharmaceutically acceptable salt or ester thereof.

In other particular embodiment, the compound of Formula (I) is 14-HDHA and the SPMs and/or SPM precursor not included in Formula (I) are 17-HDHA and 18-HEPE; or a pharmaceutically acceptable salt or ester thereof.

As used herein "SPMs and/or SPM precursors" refers to specialized pro-resolving mediators and/or precursors thereof. SPM or SPM precursor is a lipid-derived compound or substance that promotes the resolution of inflammation, e.g., it can reduce one sign or symptom of inflammation in a cell or organism.

SPMs represent a class of pro-resolving, anti-pain and anti-inflammatory lipids naturally derived from omega 3 and omega 6 fatty acids that help healing without compromising the body's ability to defend against inflammatory insults (e.g., infection or injury).[5-7] SPMs are a genus with several families of potent endogenous bioactive products derived from precursors essential fatty acids EPA, DHA, arachidonic acid (ARA) and Docosapentaenoic acid (DPA) that are biosynthesized by positional and stereospecific incorporation of one, two or three molecules of molecular oxygen into a polyunsaturated fatty acid (PUFA) using EPA, DHA, ALA and DPA as substrates into a catalyzed reaction involving fatty acid lipoxygenases, cyclooxygenase type-2, when acetylated by aspirin, and several cytochrome P450 oxidases.

As used in this invention, SPM relates to a PUFA-derived enzymatically-oxygenated derivative that has potent anti-inflammatory and resolution-activating activity and that acts as endogenous regulator of the inflammatory response to bring an inflamed tissue back towards its non-inflamed and healthy state. SPMs act as endogenous receptor ligands or allosteric modulators to potently activate cellular responses that conceitedly activate anti-inflammatory actions and expedite, stimulate, and trigger resolution of inflammation. The term "SPM precursor" refers to an enzymatically oxygenated derivative of a PUFA that requires an additional enzymatic reaction to convert it to a SPM. A SPM precursor is a more proximate substrate for the endogenous formation of an SPM than the corresponding PUFA substrate itself.

The SPMs include several families of mediators, lipoxins, resolvins (e.g., the E and D series), protectins and maresins. Examples of SPM include Resolvin E1 (RvE1; 5S,12,18-trihydroxy-eicosa-6Z,8E,10E,14Z,16E-pentaenoic acid), 18S-Resolvin E1 (18S-RvE1; 5S,12R,18S-trihydroxy-eicosa-6Z,8E,10E,14Z,16E-pentaenoic acid), 20-hydroxy-RvE1 (5S,12R,18R,20-tetrahydroxy-eicosa-6Z,8E,10E,14Z,16E-pentaenoic acid), Resolvin E2 (RvE2; 5S,18-dihydroxy-eicosa-6E,8Z,11Z,14Z,16E-pentaenoic acid), Resolvin E3 (RvE3; 17,18R-dihydroxy-eicosa-5Z,8Z,11Z,13E,15E-pentaenoic acid), 18S-Resolvin E5 (18S-RvE3; 17,18S-dihydroxy-eicosa-5Z,8Z,11Z,13E,15E-pentaenoic acid), 17,18-epoxy-eicosa-5Z,8Z,11Z,13E,15E-pentaenoic acid, Lipoxin $A_5$ (LXA$_5$; 5S,6R,15S-trihydroxy-eicosa-7E,9E,11Z,13E,17Z-pentaenoic acid), 15-epi-Lipoxin A5 (LXA5; 5S,6R,15R-trihydroxy-eicosa-7E,9E,11Z,13E,17Z-pentaenoic acid), Maresin 1 (MaR1; 7R,14S-dihydroxy-docosa-4Z,8E,10E,12Z,16Z,19Z-hexaenoic acid), 7S-Maresin 1 (7S-MaR1; 7S,14S-dihydroxy-docosa-4Z,8E,10E,12Z,16Z,19Z-hexaenoic acid), 7S,14S-diHDHA (7S,14S-dihydroxy-docosa-4Z,8E,10Z,12E,16Z,19Z-hexaenoic acid), Protectin D1 (PD1; 10R,17S-dihydroxy-docosa-4Z,7Z,11E,13E,15Z,19Z-hexaenoic acid), 10S,17S-HDHA (10S,17S-dihydroxy-docosa-4Z,7Z,11E,13Z,15E,19Z-hexaenoic acid), 14S,21S-diHDHA (14S,21S-dihydroxy-docosa-4Z,7Z,10Z,12E,16Z,19Z-hexaenoic acid), 14S,21R-diHDHA (14S,21R-dihydroxy-docosa-4Z,7Z,10Z,12E,16Z,19Z-hexaenoic acid), 14R,21S-diHDHA (14R,21S-dihydroxy-docosa-4Z,7Z,10Z,12E,16Z,19Z-hexaenoic acid), 14R,21R-diHDHA (14R,21R-dihydroxy-docosa-4Z,7Z,10Z,12E,16Z,19Z-hexaenoic acid), 13S,14S-epoxy-DHA (13S,14S-epoxy-docosa-4Z,7Z,9E,11E,16Z19Z-hexaenoic acid), 16,17S-diHDHA (16,17S-dihydroxy-docosa-4Z,7Z,10Z,12E,14E,19Z-hexaenoic acid), 16,17-epoxy-DHA (16,17-epoxy-docosa-4Z,7Z,10Z,12E,14E,19Z-hexaenoic acid), Resolvin D1 (RvD1; 7S,8R,17S-trihydroxy-docosa-4Z,9E,11E,13Z,15E,19Z-hexaenoic acid), Resolvin D2 (RvD2; 7S,16R,17S-trihydroxy-docosa-4Z,8E,10Z,12E,14E,19Z-hexaenoic acid), Resolvin D3 (RvD3; 4S,11R,17S-trihydroxy-docosa-5Z,7E,9E,13Z,15E,19Z-hexaenoic acid), Resolvin D4 (RvD4; 4S,5,17S-trihydroxy-docosa-6E,8E,10Z,13Z,15E,19Z-hexaenoic acid), Resolvin D5 (RvD5; 7S,17S-dihydroxy-docosa-5Z,8E,10Z,13Z,15E,19Z-hexaenoic acid), Resolvin 6 (RvD6; 4S,17S-dihydroxy-docosa-5E,7Z,10Z,14Z,16E,19Z-hexaenoic acid), aspirin-triggered Resolving D1 (AT-RvD1; 7S,8R,17R-trihydroxy-docosa-4Z,9E,11E,13Z,15E,19Z-hexaenoic acid), aspirin-triggered Resolvin D2 (AT-RvD2; 7S,16R,17R-trihydroxy-docosa-4Z,8E,10Z,12E,14E,19Z-hexaenoic acid), aspirin-triggered Resolvin D3 (AT-RvD3; 4S,11,17R-trihydroxy-docosa-5Z,7E,9E,13Z,15E,19Z-hexaenoic acid), aspirin-triggered Resolvin D4 (AT-RvD4; 4S,5,17R-trihydroxy-docosa-6E,8E,10Z,13Z,15E,19Z-hexaenoic acid), aspirin-triggered. Resolvin D5 (AT-RvD5; 7S,17R-dihydroxy-docosa-5Z,8E,10Z,13Z,15E,19Z-hexaenoic acid), aspirin-triggered Resolvin D6 (AT-RvD6; 4S,17R-dihydroxy-docosa-5E,7Z,10Z,14Z,16E,19Z-hexaenoic acid), 7S,17S-diHDPA n-3 (7S,17S-dihydroxy-docosa-8E,10Z,13Z,15Z,19Z-pentaenoic acid (ω-3)), Lipoxin $A_4$ (LXA$_4$; 5S,6R,15S-trihydroxy-eicosa-7E,9E,11Z,13E-tetraenoic acid), 15-epi-Lipoxin $A_4$ (15-epi-LXA$_4$; 5S,6R,15R-trihydroxy-eicosa-7E,9E,11Z,13E-tetraenoic acid), delta 12-prostaglandin $J_2$ (delta12-PGJ$_2$; 11-oxo-15S-hydroxy-prosta-5Z,9,12E-trienoic acid), 15-deoxy-delta12,14-prostaglandin $J_2$ (15-deoxy-delta12,14-PGJ$_2$; 11-oxo-prosta-5Z,9,12E,14E-tetraenoic acid), 11(12)-epoxy-eicosatetraenoic acid (11(12)-EpETE; 11(12)-epoxy-eicosa-5Z,8Z,14Z,17Z-tetraenoic acid), 17(18)-epoxy-eicosatetraenoic acid (17(18)-EpETE; 17(18-epoxy-eicosa-5Z,8Z,11Z,14Z-tetraenoic acid), 19(20)-epoxy-docosapentaenoic acid (19(20)-EpDPE; 19(20)-epoxy-docosa-4Z,7Z10Z, 13Z,16Z-pentaenoic acid), 10S,17S-HDPA n-6 (10S,17S-dihydroxy-docosa-4Z,7Z,11E,13Z,15E-pentaenoic acid), 7,17-HDPA n-6 (7,17-dihydroxy-docosa-4Z,8E,10Z,13Z,15E-pentaenoic acid), 7,14-HDPA n-6 (7,14-dihydroxy-docosa-4Z,8E,10Z,12Z,16Z-pentaenoic acid), 10S,17S-HDPA n-6 (10S,17S-dihydroxy-docosa-7Z,11E,13Z,15E,19Z-pentaenoic acid), and/or 7, 17-HDPA (7,17-dihydroxy-docosa-8E,10Z,13Z,15E,19Z-pentaenoic acid).

Examples of SPM precursors include 5S-HEPE (5S-hydroxy-eicosa-6E,8Z,11Z,14Z,17Z-pentaenoic acid); 11S-HEPE (11S-hydroxy-eicosa-5Z,8Z,12E,14Z,17Z-pentaenoic acid); 12S-HEPE (12S-hydroxy-eicosa-5Z,8Z,10E,14Z,17Z-pentaenoic acid); 12R-HEPE (12R-hydroxy-eicosa-5Z,8Z,10E,14Z,17Z-pentaenoic acid); 15S-HEPE (15S-hydroxy-eicosa-5Z,8Z,11Z,13E,17Z-pentaenoic acid); 4S-HDHA (4S-hydroxy-docosa-5E,7Z,10Z,13Z,16Z,19Z-hexaenoic acid); 7S-HDHA (7S-hydroxy-docosa-4Z,8E,10Z,13Z,16Z,19Z-hexaenoic acid); 7R-HDHA (7R-hydroxy-docosa-4Z,8E,10Z,13Z,16Z,19Z-hexaenoic acid); 10S-HDHA (10S-hydroxy-docosa-4Z,7Z,11E,13Z,16Z,19Z-hexaenoic acid); 11S-HDHA (11S-hydroxy-docosa-4Z,7Z,9E,13Z,16Z,19Z-hexaenoic acid); 14S-HDHA (14S-hydroxy-docosa-4Z,7Z,10Z,12E,16Z,19Z-hexaenoic acid); 14R-HDHA (14R-hydroxy-docosa-4Z,7Z,10Z,12E,16Z,19Z-hexaenoic acid); 20S-HDHA (20S-hydroxy-docosa-4Z,7Z,10Z,13Z,16Z,19Z-hexaenoic acid); 17S-HDPAn-6 (17S-hydroxy-docosa-4Z,7Z,10Z,13Z,15E-pentaenoic acid); 14S-HDPAn-6 (14S-hydroxy-docosa-4Z,7Z,10Z,12E,16Z-pentaenoic acid); 10S-HDPAn-6 (10S-hydroxy-docosa-4Z,7Z,11E,13Z,16Z-pentaenoic acid); 17S-HDPAn-3 (17S-hydroxy-docosa-7Z,10Z,13Z,15E,19Z-pentaenoic acid); 14S-HDPAn-3 (17S-hydroxy-docosa-7Z,10Z,12E,16Z,19Z-pentaenoic acid); 10S-HDPAn-6 (10S-hydroxy-docosa-7Z,11E,13Z,16Z,19Z-pentaenoic acid); 15S-HETE (15S-hydroxy-eicosa-5Z,8Z,11Z,13E-tetraenoic acid); and/or 15R-HETE (15R-hydroxy-eicosa-5Z,8Z,11Z,13E-tetraenoic acid). Such mediators and methods of producing them are described in, for example, U.S. Pat. Nos. 7,615,576; 5,441,951; 6,887,901; 7,737,178; 7,595,341; 7,378,444; 7,585,856; 6,703,423; 7,700,650; 7,812,054; 7,132,451; U.S. Patent Publications 2010/0105772; 2010/0105773; 2009/0156673; 2006/0293288; 2003/0166716, 2008/0312323, 20140079631, 20150126602, 20180200375, and 2018/0256597; and Serhan et al. FASEB Journal 2012 26.

SPMs and SPM precursors also include, in addition to the SPMs and SPM precursors listed above, other mono-, di-, and tri-hydroxylated and epoxygenated derivatives of the above mentioned polyunsaturated fatty acids, which possess anti-inflammatory and proresolving activities. In addition, the SPMs and SPM precursors may be present as esters and amides, which are within the scope of SPMs and SPM precursors in this invention. The esters can be natural esters such as triglycerides, diglycerides, monoglycerides, and phospholipids, as well as esters prepared during the industrial processes commonly employed in the fish oil industry permitting the concentration of EPA and DHA from crude and refined fish oils, in particular the form of ethyl esters.

In other embodiment, the treatment site can comprise the vulvar vestibule, external vulva, vestibule, cervix or vagina.

In general, the compounds or compositions can be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the pro-resolving mediator compounds of the present disclosure for a given disease. Thus, the compounds or compositions of the present disclosure can be administered as pharmaceutical formulations including those suitable for topical, vaginal, oral (including buccal and sub-lingual), rectal, nasal, pulmonary, or parenteral (including intramuscular, intraarterial, intrathecal, subcutaneous and intravenous) administration or in a form suitable for administration by inhalation or insufflation. In certain aspects, the manner of administration is topical, vaginal, or transdermal using a convenient daily dosage regimen which can be adjusted according to the degree of affliction.

In particular, topical and/or transdermal treatment using the compounds or compositions is preferred for local control of disease states and inflammatory cascade states for reducing or preventing lower genital tract pain in a subject, such as LPV, while insuring that any unwanted side effects are minimized and curtailed.

To that end, the pharmaceutical compositions of the present disclosure can be suitable for topical administration. In that case, the pharmaceutical compositions comprise one or more pro-resolving mediators, a pharmaceutically acceptable topical carrier, and optionally a permeation enhancer. In some aspects, the permeation enhancer can comprise a base. The base can be present at a concentration sufficient to provide a formulation pH in the range of approximately 7.5 to 13.0. The pharmaceutical composition can be aqueous. The aqueous pharmaceutical composition can be a cream, gel, lotion, paste, or solution.

Various skin-permeation enhancing agents are known in the art and can be used in this invention. Examples of suitable enhancers include, but are not limited to, ethers such as diethylene glycol monoethyl ether (available commercially as TRANSCUTOL) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and $C_{10}$ MSO may also be used.

Other suitable enhancers include those lipophilic co-enhancers typically referred to as "plasticizing" enhancers, i.e., enhancers that have a molecular weight in the range of about 150 to 1000, an aqueous solubility of less than about 1 wt. %, preferably less than about 0.5 wt. %, and most preferably less than about 0.2 wt. %. The Hildebrand solubility parameter of plasticizing enhancers is in the range of about 2.5 to about 10, preferably in the range of about 5 to about 10. Such enhancers are described in, e.g., U.S. Pat. No. 6,586,000, and WO 01/43775. Preferred lipophilic enhancers are fatty esters, fatty alcohols, and fatty ethers. Examples of specific and most preferred fatty acid esters include methyl laurate, ethyl oleate, propylene glycol monolaurate, propylene glycerol dilaurate, glycerol monolaurate, glycerol monooleate, isopropyl n-decanoate, and octyldodecyl myristate. Fatty alcohols include, for example, stearyl alcohol and oleyl alcohol, while fatty ethers include compounds wherein a diol or triol, preferably a $C_2$-$C_4$ alkane diol or triol, are substituted with one or two fatty ether substituents. Additional permeation enhancers are known in the art of topical drug delivery. See, e.g., Percutaneous Penetration Enhancers, Smith et al., editors (CRC Press, 1995).

A formulation described herein may be in any form suitable for topical application, for example to the skin (e.g., the external vulva, vestibule, or vagina) and surrounding tissues. It may comprise, for example, a cream, lotion, solution, gel, ointment, paste, plaster, paint, bioadhesive, or the like, and/or may be prepared to contain liposomes, micelles, and/or microspheres. Such a formulation may be aqueous, i.e., contain water, or may be nonaqueous and optionally used in combination with an occlusive overlayer so that moisture evaporating from the body surface is maintained within the formulation upon application to the body surface and thereafter.

Formulations of the invention may optionally contain a pharmaceutically acceptable viscosity enhancer and/or film former. A viscosity enhancer increases the viscosity of the formulation to inhibit its spread beyond the site of application. Balsam Fir (Oregon) is an example of a pharmaceutically acceptable viscosity enhancer. A film former, when it dries, forms a protective film over the site of application. The film inhibits removal of the active ingredient and keeps it in contact with the site being treated. An example of a film former that is suitable for use in this invention is Flexible Collodion, USP. As described in Remington: The Science and Practice of Pharmacy, 19th Ed. (Easton, Pa.: Mack Publishing Co., 1995), at page 1530, collodions are ethyl ether/ethanol solutions containing pyroxylin (a nitrocellulose) that evaporate to leave a film of pyroxylin. A film former may act additionally as a carrier. Solutions that dry to form a film are sometimes referred to as paints.

Ointments, as is well known in the art of pharmaceutical formulation, are semisolid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes:

oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight; again, see Remington: The Science and Practice of Pharmacy for further information.

Creams, as also well known in the art, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

As will be appreciated by those working in the field of pharmaceutical formulation, gels are semisolid, suspension-type systems. Single-phase gels contain organic macromolecules distributed substantially uniformly throughout the carrier liquid, which is typically aqueous, but also, preferably, contain an alcohol and, optionally, an oil. Preferred "organic macromolecules," i.e., gelling agents, are cross-linked acrylic acid polymers such as the "carbomer" family of polymers, e.g., carboxypolyalkylenes that may be obtained commercially under the CARBOPOL. Also preferred are hydrophilic polymers such as polyethylene oxides, polyoxyethylene-polyoxypropylene copolymers, and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions are preparations to be applied to the skin surface without friction, and are typically liquid or semiliquid preparations in which particles, including the active agent, are present in a water or alcohol base. Lotions are usually suspensions of solids, and preferably, for the present purpose, comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Pastes are semisolid dosage forms in which the active agent is suspended in a suitable base. Depending on the nature of the base, pastes are divided between fatty pastes or those made from a single-phase aqueous gels. The base in a fatty paste is generally petrolatum or hydrophilic petrolatum or the like. The pastes made from single-phase aqueous gels generally incorporate carboxymethylcellulose or the like as a base.

Plasters are comprised of a pasty mixture that is spread on the body, either directly or after being saturated into a base material such as cloth. Medications, including the bases of the invention, may be dissolved or dispersed within the plaster to make a medicated plaster.

Bioadhesives are preparations that adhere to surfaces of body tissues. Polymeric bioadhesive formulations are well known in the art; see, for example, Heller et al., "Biodegradable polymers as drug delivery systems," in Chasin, M. and Langer, R., eds.: Dekker, New York, pp. 121-161 (1990); and U.S. Pat. No. 6,201,065. Suitable non-polymeric bioadhesives are also known in the art, including certain fatty acid esters (U.S. Pat. No. 6,228,383).

Formulations described in this invention may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the instant invention include cationic (positively charged), anionic (negatively charged) and neutral preparations. Cationic liposomes are readily available. For example, N[1-2,3-dioleyloxy)propyl]-N,N,N-triethylammonium (DOTMA) liposomes are available under the tradename Lipofectin®. (GIBCO BRL, Grand Island, N.Y.). Similarly, anionic and neutral liposomes are readily available as well, e.g., from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with DOTMA in appropriate ratios. Methods for making liposomes using these materials are well known in the art.

Micelles are known in the art to be comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10 and nonoxynol 30. Micelle formulations can be used in conjunction with the present invention either by incorporation into a topical or transdermal delivery system, or into a formulation to be applied to a target site (e.g., vestibule) and surrounding tissues.

Microspheres, similarly, may be incorporated into the present formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids. Preparation of microspheres is well known in the art and described in the pertinent texts and literature.

Various additives known in the art may be included in the topical formulations. For example, solvents, including relatively small amounts of alcohol, may be used to solubilize certain formulation components. The present formulations may also include conventional additives such as opacifiers, antioxidants, fragrance, colorants, gelling agents, thickening agents, stabilizers, surfactants, and the like. Other agents may also be added, such as antimicrobial agents, to inhibit growth of microbes such as bacteria, yeasts, and molds. Exemplary antimicrobial agents are typically selected from the group consisting of the methyl and propyl esters of p-hydroxybenzoic acid (i.e., methyl and propyl paraben), sodium benzoate, sorbic acid, imidurea, and combinations thereof.

In one embodiment, compounds of Formula (I) or compositions thereof are topically administered.

The compounds of Formula (I) described above and related compositions are useful in methods of treating various inflammatory disorders or conditions. Varieties or combinations of this therapy include, though are not limited to the following exemplary applications: a topical/transdermal spray using a radiating pump dispenser; a topical/transdermal salve/balm rubbed into the treated area; a topical/transdermal wound cleansing rinse; a topical/transdermal roll-on for pain relief; an impregnated mini-sponge individually hermetically sealed with said composition that can be reconstituted with water; a wound powder composed of micronized, freeze dried material, and a time-released epidermal/topical patch for staged and sequential delivery of said composition for site-specific application.

The therapeutic composition may preferably be administered as needed. For example, for severe conditions, about 1-4 times per day on a daily basis can be used. In addition, the therapeutic composition may alternatively be administered on a weekly, bi-weekly, tri-weekly, weekly or monthly basis until the condition is treated or remediated as desired. Furthermore, the administration may initially begin on a daily basis and then, in response to clinical improvement, transition to a weekly, monthly, etc. administration. Rather than being used solely as a treatment aid, the composition of the present invention may also be used to maintain a user in pain free condition.

In certain embodiments, the effective dose of a composition comprising one or more pro-resolving mediators as described herein can be administered to a patient once. In certain embodiments, the effective dose of a composition comprising a pro-resolving mediator can be administered to a patient repeatedly. Patients can be administered a therapeutic amount of a composition comprising a pro-resolving mediator at 0.0001 mg/kg to 100 mg/kg, such as 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg or 50 mg/kg. A composition comprising a pro-resolving mediator can be administered over a period of time, such as over a 5 minute, 10 minute, 15 minute, 20 minute, or 25 minute period. The administration is repeated, for example, on a regular basis, such as hourly for 3 hours, 6 hours, 12 hours or longer or such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of a composition comprising a pro-resolving mediator can reduce levels of a marker or symptom of, for example, inflammation by at least 10%, at least 15%, at least 20%, at least 25%, at least 30%, at least 40%, at least 50%, at least 60%, at least 70%, at least 80% or at least 90% or more.

Treating vulvodynia and other female genital tract conditions entails vaginal or perivaginal administration. To that end, vaginal or perivaginal dosage forms may include vaginal suppositories, creams, ointments, liquid formulations, pessaries, tampons, gels, pastes, foams or sprays. The suppository, cream, ointment, liquid formulation, pessary, tampon, gel, paste, foam or spray for vaginal or perivaginal delivery comprises a therapeutically effective amount of the selected active agent and one or more conventional nontoxic carriers suitable for vaginal or perivaginal drug administration. The vaginal or perivaginal forms of the present invention may be manufactured using conventional processes as disclosed in Remington: The Science and Practice of Pharmacy, supra (see also drug formulations as adapted in U.S. Pat. Nos. 6,515,198; 6,500,822; 6,417,186; 6,416,779; 6,376,500; 6,355,641; 6,258,819; 6,172,062; and 6,086,909). The vaginal or perivaginal dosage unit may be fabricated to disintegrate rapidly or over a period of several hours. The time period for complete disintegration may be in the range of from about 10 minutes to about 6 hours, e.g., less than about 3 hours.

The compounds of Formula (I) described above can be included in other suitable compositions or kits. Examples of such compositions and kits include a birth control device or agent, a feminine sanitary product such as a douche, sanitary pad or, preferably a tampon, a vaginal or an anal suppository, or an enema, all of which may provide with one or more other therapeutic agents (e.g., an antimicrobial agent, antiviral agent, and anti-STD agent), and all of which may be provided as sustained release compositions (e.g., in a sustained release device).

In addition to vulvodynia, examples of other female genital tract conditions that can be treated include lichen planus, lichen sclerosus, and atrophic vulvovaginitis associated with breast cancer.

Lichen planus may present as one of two types: (1) "classic", consisting of sharply demarcated, flat-topped plaques on oral and genital membranes and (2) "erosive", consisting of an erosive, erythematous lesion originating in the vestibule and variably extending up the vaginal canal. Erosive lichen planus is commonly characterized, symptomatically, by chronic spontaneous burning pain.

Lichen sclerosus is visually characterized by depigmentation, a loss of mucocutaneous markings, and submucosal hemorrhage. Reduced elasticity of the skin surface may result in fissuring at the perineal body. Lichen sclerosus may involve the labia minora, clitoris, interlabial sulcus, and inner portion of labia majora and perianal areas as well. Circumferential depigmentation of the vaginal introitus and the adjacent perianal region with lichen sclerosus has been characterized by the descriptive term "keyhole distribution".

Desquamative inflammatory vaginitis is characterized by burning pain, visible inflammation and increased vaginal discharge on clinical exam, and evidence of parabasal cells, microscopically. A key diagnostic hallmark is the finding of parabasal cells with inflammation in the presence of adequate estrogenization, and absence of infectious etiology on microscopic study, or other laboratory method.

Atrophic vulvovaginitis associated with breast cancer is characterized by burning pain and painful intercourse. On clinical exam, there is loss of vaginal rugal architecture, dryness, and visible pallor to the mucosa. The use of topical estrogen for treatment has been controversial in this group of cancer survivors.

Other conditions that can be treated include chronic pruritus. The problem of pruritus can be as debilitating as pain in many with lichen sclerosus and lichen planus. It is mediated by a similar neural fiber (c fiber) as allodynia although by microneurography pruritus is mediated through a distinct neural subset. The mediators (inflammosomes) of pruritus appear to be similar to the pain mediators As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition (such as pain). The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms (such as pain) or markers (such as cytokines), but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of inflammation, delay or slowing of inflammation, and amelioration or palliation of inflammation.

The term "topical," as used herein, refers to the administration of the compositions of the invention to the skin and underlying tissues, as well as to administration to the mucosa and underlying tissues.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to a reference level, or any decrease between 10-99% as compared to the absence of a given treatment.

When the terms "prevent", "preventing", and "prevention" are used herein in connection with a given treatment for a given condition, they mean that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have "prevented" the condition if it is given during exposure of a patient to a stimulus that would have been expected to produce a given manifestation (such as pain) of the condition, and results in the patient's experiencing fewer and/or milder symptoms of the condition than otherwise expected. For example, a treatment can "prevent" inflammation by resulting the patient's displaying only mild overt symptoms of the inflammation; it does not imply that there must have been no inflammation or no production of pro-inflammatory cytokines, inflammation mediators and/or the related downstream cellular events.

As used herein, the term "enriched" refers to a composition (e.g., an oil) containing one or more compounds of Formula (I) when it contains a higher level of this or these compounds than the source from which it was made.

As used herein, the phrase "therapeutically effective amount", "effective amount" or "effective dose" refers to an amount that provides a therapeutic or aesthetic benefit in the treatment, prevention, or management of, for example, pain, inflammation or wound healing, e.g. an amount that provides a statistically significant decrease in at least one symptom, sign, or marker of pain, inflammation, and/or wound healing. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. As used herein, the term "pharmaceutical composition" refers to the active agent in combination with a pharmaceutically acceptable carrier commonly used in the pharmaceutical industry.

As used herein, a "subject" means a human or an animal. Preferably, the subject is a mammal. The mammal can be a human, non-human primate, mouse, rat, dog, cat, horse, or cow, but are not limited to these examples. Mammals other than humans can be advantageously used, for example, as subjects that represent animal models of, for example, inflammation. In addition, the methods described herein can be used to treat domesticated animals and/or pets.

A subject can be one who has been previously diagnosed with or identified as suffering from or having a condition in need of treatment (e.g., inflammation or other pain-causing conditions) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. For example, a female subject may be treated as described herein to remediate pain after a disease (e.g., atrophic vulvovaginitis associated with breast cancer) is established or prior to secondary exposure events (for example treat for a few weeks before attempting intercourse again).

As used herein, "inflammation" refers to the complex biological response to harmful stimuli, such as pathogens, damaged cells, or irritants. Inflammation is a protective attempt by the organism to remove the injurious stimuli as well as initiate the healing process for the tissue. Accordingly, the term "inflammation" includes any cellular process that leads to the production of pro-inflammatory cytokines, inflammation mediators and/or the related downstream cellular events resulting from the actions of the cytokines thus produced, for example, fever, fluid accumulation, swelling, abscess formation, and cell death. Pro-inflammatory cytokines and inflammation mediators include, but are not limited to, IL-1-alpha, IL-1-beta, IL-6, IL-8, IL-11, IL-12, IL-17, IL-18, TNF-alpha, leukocyte inhibitory factor (LIF), IFN-gamma, Oncostatin M (OSM), ciliary neurotrophic factor (CNTF), TGF-beta, granulocyte-macrophage colony stimulating factor (GM-CSF), and chemokines that chemoattract inflammatory cells. Inflammation can include both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

The term "esters" are referred to all esters than can be prepared by the reaction of a compound of Formula (I) as free acid or an activated form thereof, with other compound according "$R_1$" definition. In addition, "esters" for the present invention are esters such as triglycerides, diglycerides, monoglycerides, and phospholipids. For clarification, one, two or three compounds of Formula (I) can be bonded to a molecule of glycerol or phospholipid, as well as esters prepared during the industrial processes commonly employed in the fish oil industry permitting the concentration of EPA and DHA from crude and refined fish oils, in particular the form of ethyl esters.

The term "Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne.

Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

The term "Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

The term "Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxazine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

The term "Heteroarylalkyl" by itself or as part of another substituent refers to an acyclic alkyl group in which one of the hydrogen atoms bonded to a carbon atom, typically a terminal or sp3 carbon atom, is replaced with a heteroaryl group. Where specific alkyl moieties are intended, the nomenclature heteroaryl alkanyl, heteroarylakenyl and/or heteroaryl alkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

The terms "Heteroalkyl," Heteroalkanyl," "Heteroalkenyl," "Heteroalkynyl," "Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteratoms or heteroatomic groups. Typical heteroatoms and/or heteroatomic groups which can replace the carbon atoms include, but are not limited to, —O—, —S—, —S—O—, —NR'—, —PH—, —S(O)—, —S(O)2-, —S(O) NR'—, —S(O)2NR'—, and the like, including combinations thereof, where each R' is independently hydrogen or (C1-C6) alkyl.

The terms "Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., mopholin-3-yl, morpholin-4-yl, etc.), piperazinyl (e.g., piperazin-1-yl, piperazin-2-yl, etc.), and the like.

EXAMPLES

Example 1

In this example, a fibroblast-based in vitro LPV model was established. Briefly, fibroblast strains were obtained from two regions (FIG. 1) of the lower genital tract of localized provoked vulvodynia (LPV) cases and pain-free controls in the manner described in Falsetta et al. Am J Obstet Gynecol 2015, vol. 213, pp. 38 e1-12 and Foster et al., Pain 2015, vol. 156, pp. 386-96.

Over 30 paired fibroblast strains obtained from LPV-afflicted cases (fulfilling Friedrich's Criteria)[25] and age/race-matched (critical variables influencing LPV),[26, 27] pain-free controls were obtained. All subjects who contributed to the library were premenopausal, denied oral corticosteroids, non-steroidal, immunomodulatory, or anti-inflammatory medication use, and reported an absence of systemic/cutaneous inflammatory conditions at the time of sample collection. Mechanical pain thresholds were determined (via a method of limits) (0.5-5 N) using a Wagner algometer. Fibroblast identity was confirmed by microscopy and fibroblast markers (vimentin, collagen); only low passage (~4) cells are used.

The fibroblast strains were then challenged with stimuli such as Candida ablicans (FIG. 3A). It was found that fibroblasts taken from the painful vestibule of LPV patients produced high levels of IL-6 when infected with Candida ablicans, even at doses lower than those normally detectable within the vulvovaginal milieu, while fibroblasts from non-painful external vulva are weakly responsive (FIG. 3A). C. albicans is a chief cause of vulvovaginal yeast infection,[19-22] and chronic yeast infection has been cited as a preceding factor in >70% LPV patients.[23] Repeated vulvovaginal infection in mice induces vulvar allodynia and regional hyperinnervation, simulating vulvodynia findings.[24] Recent studies[3,4,13] have shown that LPV is associated with inflammatory dysregulation, despite the fact LPV does not present as a classical inflammatory disease. The cardinal signs of inflammation are not pronounced or are vaguely present in both healthy and LPV-afflicted women, although the infiltration and organization of immune cells is distinctively different in LPV versus healthy patients.[17]

In addition, it was found that there was a site-specific response to live yeast infection, whereby fibroblasts from sites of pain within the vulvar vestibule are inherently sensitive to yeast/yeast products and produce elevated levels of pro-pain/pro-inflammatory mediators compared to fibroblasts from non-painful sites of the external vulva (FIG. 3B). Furthermore, this response appeared to be an exacerbation of a normal inflammatory response, as fibroblasts from the vestibule of healthy women showed a similar, albeit reduced, response to Zymosan (yeast cell wall product; FIG. 3B). More importantly, there was a strong connection between LPV pain and inflammation; pain in LPV patients was directly correlated with the production of pro-inflammatory and pro-pain mediators by fibroblasts cultured from biopsies of painful sites, when exposed to live yeast (FIG. 3C).

Example 2

In this example, assays were carried out to investigate the ability of compounds of Formula (I) to reduce pro-inflammatory and pro-pain mediator production from primary human cells in the in vitro LPV model described in Example 1.

The inventors used one of two treatment regimens proven effective in vulvar fibroblasts and other cells at low/nanomolar concentrations (1-100 nM): 1) overnight pre-treatment, followed by another treatment 30 min prior to stimulation with pro-inflammatory stimuli for 48 hr with a third dose of a compound of Formula (I) at 24 hr post-challenge, or 2) post-treatment a compound of Formula (I) after a 30 min pre-treatment with inflammatory stimuli, followed by a booster dose 18 hr later. Both treatment regimens are of interest, as compounds of Formula (I) are active throughout the inflammatory process.[5-7] Even the compound of Formula (I) administered after LPV onset are likely to prevent the worsening or spread of LPV pain.

The data show that compounds of Formula (I) were highly effective in reducing pro-inflammatory mediators linked to pain in human vulvar fibroblasts treated with relevant pro-inflammatory stimuli using a pre-treatment strategy. Maresin 1 and epi-Maresin 1 significantly reduced prostaglandin $E_2$ ($PGE_2$; FIG. 4A) and interleukin-6 (IL-6; FIG. 4B) production by both vestibular and external vulvar fibroblasts. Maresin 1 was also tested using the post-treatment regimen and found both significantly reduced IL-6 and $PGE_2$ levels under this strategy (FIGS. 4C and 4D).

Next, compounds of Formula (I) are effective in reducing IL-6 and $PGE_2$ production (e.g., Maresin 1) are investigated in similar screen. Live C. albicans yeast, Zymosan, bradykinin, and IL-1β are used as different classes of inflammatory activators, which have been shown to induce the production of pro-inflammatory mediators in vulvar fibroblasts.[3, 4, 13, 15] Pro-inflammatory mediator levels are measured using ELISAs, EIAs, and Luminex assays. Compounds of Formula (I) are effective in reducing more than one pro-inflammatory mediator in at least 2 tests move on for further testing using a preclinical mouse model. Congruent with the above supporting results showing several compounds of Formula (I) were effective in reducing pro-inflammatory mediator production, inventors expect to identify several additional compounds that are highly effective. Compounds of Formula (I) meeting criteria for further testing will be tested for their ability to reduce pain and inflammatory endpoints in a mouse model of LPV as shown in the examples below.

Prior to this work, no therapeutic agents effective in reducing the pro-inflammatory/pro-pain mediators associated with LPV had been identified. Therefore, this work represents a significant step forward in identifying potential therapeutic agents that could not only reduce excessive pro-inflammatory signaling in the context of LPV, but also in other chronic inflammatory conditions.

Example 3

In this example a compound of Formula (I) is tested for their ability to reduce pain and inflammatory endpoints in a mouse model of LPV. Only recently has an initial animal model of LPV been developed.[24] This original model has not been used for the preclinical testing of therapeutic agents. Preclinical testing is an essential step in the development of new effective FDA-approved therapies, which are sorely needed for LPV.[28, 29] Therefore, there is an urgent unmet need for a preclinical animal model that accurately reflects human LPV that could be used prior to human clinical trials. Congruent with this need, this optimized mouse model of LPV is ideal for the task of preclinical testing of therapeutic agents, as evidenced by strong supporting data.

Inventors first confirmed that mouse vulvar tissues responded to compounds of Formula (I) treatment in vitro by culturing mouse vulvar explants (4 mm punch biopsy). The explants were stimulated with IL-1β, and then assays were carried to assess the ability of Maresin 1 to reduce $PGE_2$ production under the established pre-treatment regimen.

Figure 5:
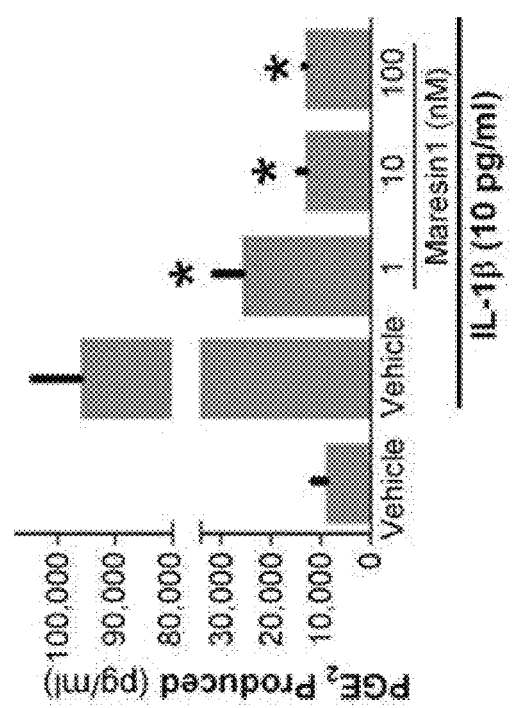
FIG. 5 is a diagram showing that compounds of Formula (I) (F (I)) inhibit $PGE_2$ production from mouse vulvar tissue. Mouse vulvar tissue (4 mm punch biopsies) was collected and bisected then pre-treated in culture medium with either Maresin 1 at indicated concentrations for 18 hours, followed by an additional 18 hours stimulation with IL-1β (10 pg/ml). Culture medium was collected and analyzed for $PGE_2$ content. Mean+/−SEM; n=3 replicate cultures. ANOVA * $p<0.05$ vs. vehicle.

It was found that enhanced $PGE_2$ responses following IL-1β treatment were significantly suppressed with Maresin 1 over a range of doses, as low as 1 nM (FIG. 5). These results confirmed that the mouse vulva responded to treatment, akin to human fibroblasts. It was also determined that these mice expressed several SPM receptors (e.g., ALX, GPR18). Therefore, inventors proceeded with testing responses to compounds of Formula (I) in the mouse model.

Figure 6:
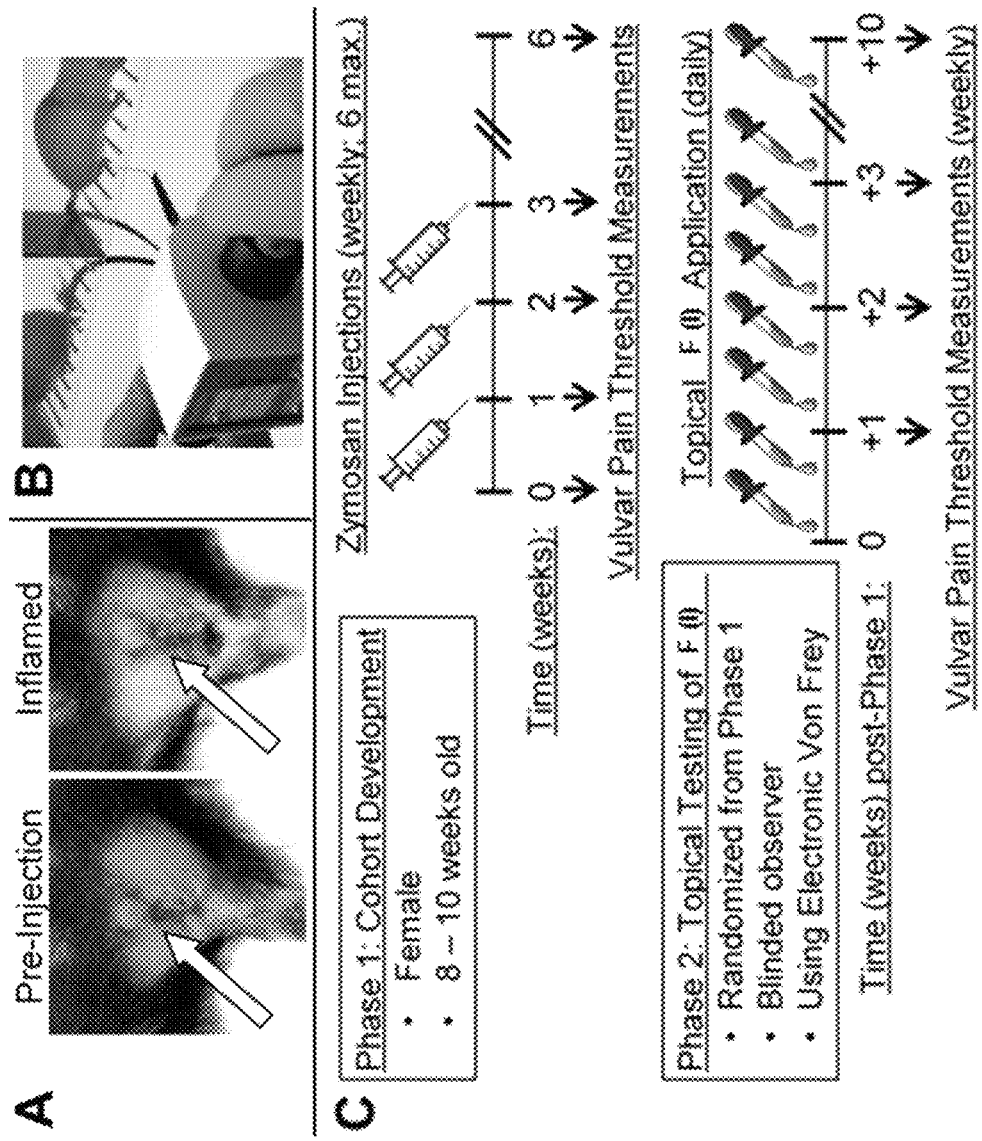
FIGS. 6A, 6B and 6C are a set of photographs and diagrams showing pain testing for in vivo mouse vulvodynia model. Panel A: After Zymosan injection, inflammation and redness become apparent. Arrow indicates injection site. Panel B: Image showing how an electronic von Frey hair (Mousemet) is used to apply force to the mouse vulva. Panel C: Schematic of in vivo mouse model to establish then resolve vulvar allodynia.

In the mouse model, Zymosan (a pro-inflammatory yeast cell wall preparation) was used to induce sustained vulvar allodynia, measured by pain threshold testing. Inventors initially used a manual von Frey system (MvF)[24], but later switched to an electronic system as detailed herein. MvF employed a series of "hairs" of different thicknesses/rigidity that exert differing forces when applied to the injection site, located at the midline posterior vulvar (between the vaginal opening and anus) (FIG. 6A). The hair was applied perpendicular to the vulvar surface with a gradually increasing force within a range of 0.100 g to 4.0 g (FIG. 6B). A positive response was defined as either a clear reflexive, all 4 extremity extension, jump, or immediate grooming of the vulva in response to vulvar stimulus. To determine the MvF threshold, the "up down method" was followed.[30] During allodynia induction, the mice receive weekly injections of Zymosan (10 μg/ml in 10 μl saline) for a maximum of 6 injections, until a >33% reduction in pain threshold is observed for two consecutive weeks of testing (FIG. 6C). Pain threshold testing was performed at the same time every week, immediately prior to Zymosan injection; after the first two weeks of injections, a determination of threshold change was performed after pain testing to determine which mice would receive additional Zymosan injections. Saline injections, which contain no pro-inflammatory agent, served as the negative control.

Figure 7:
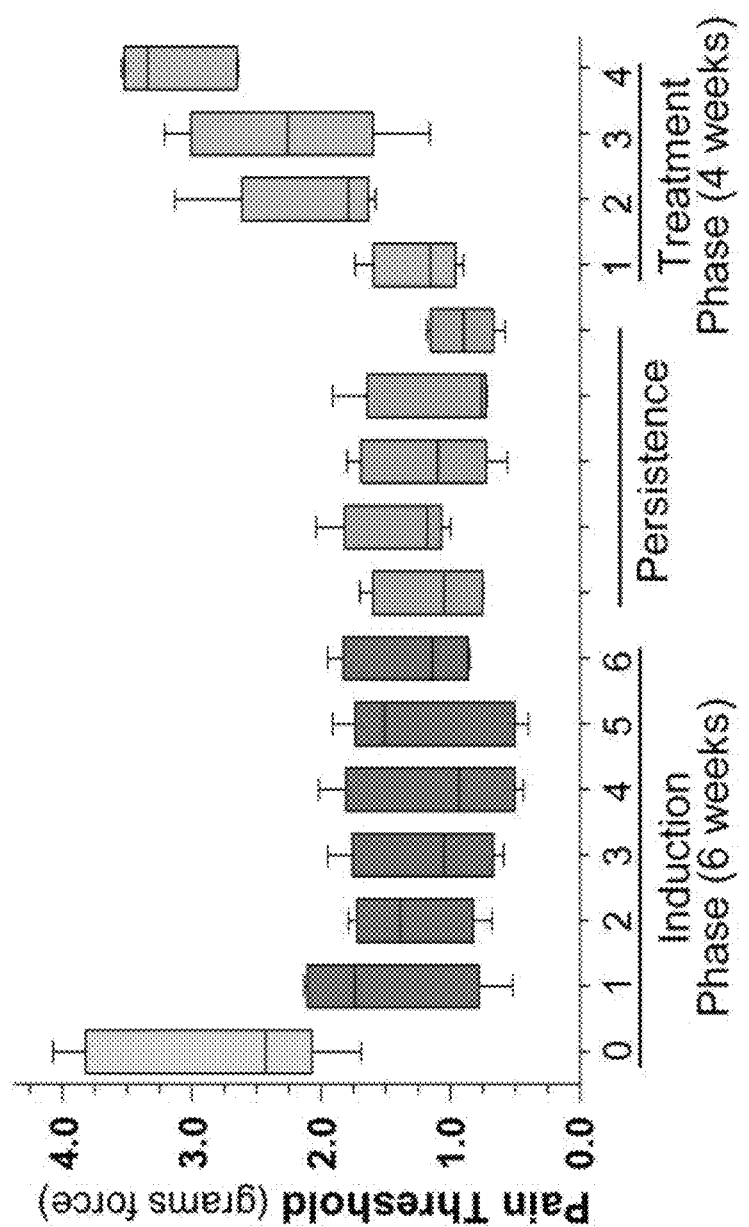
FIG. 7 is a diagram showing representative pain profile for a C57BL/6 mouse. This boxplot series shows median threshold values for a representative mouse over the induction, persistence, and treatment phases. Measures collected each week were tightly distributed, and thresholds were reduced >33% and maintained until treatment with Maresin 1, when values returned to baseline.
Figure 8:
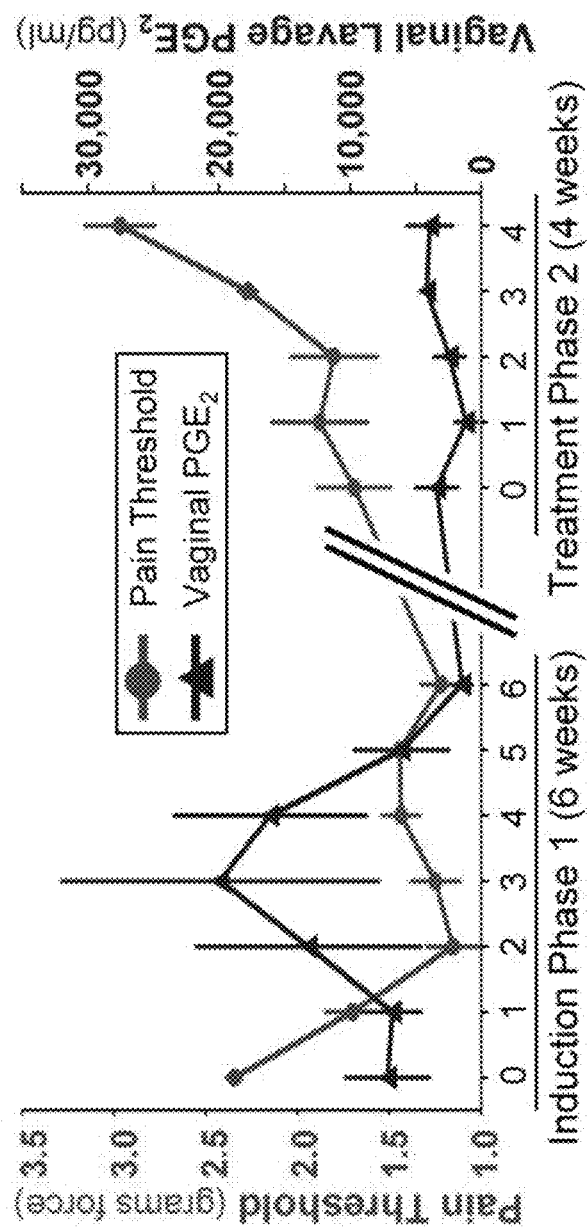
FIG. 8 is a diagram showing that $PGE_2$ in vaginal lavage is associated with pain threshold. After induction of allodynia for up to 6 weeks (indicated by reduced pain threshold, red line), Maresin 1 was applied to C57BL/6 mouse vulvas to reduce pain and increase pain threshold. $PGE_2$ content in vaginal lavage samples (blue line) rapidly increases during the induction phase, indicating pain-associated inflammation waning with treatment. SEM shown, n=8.
Figure 9:
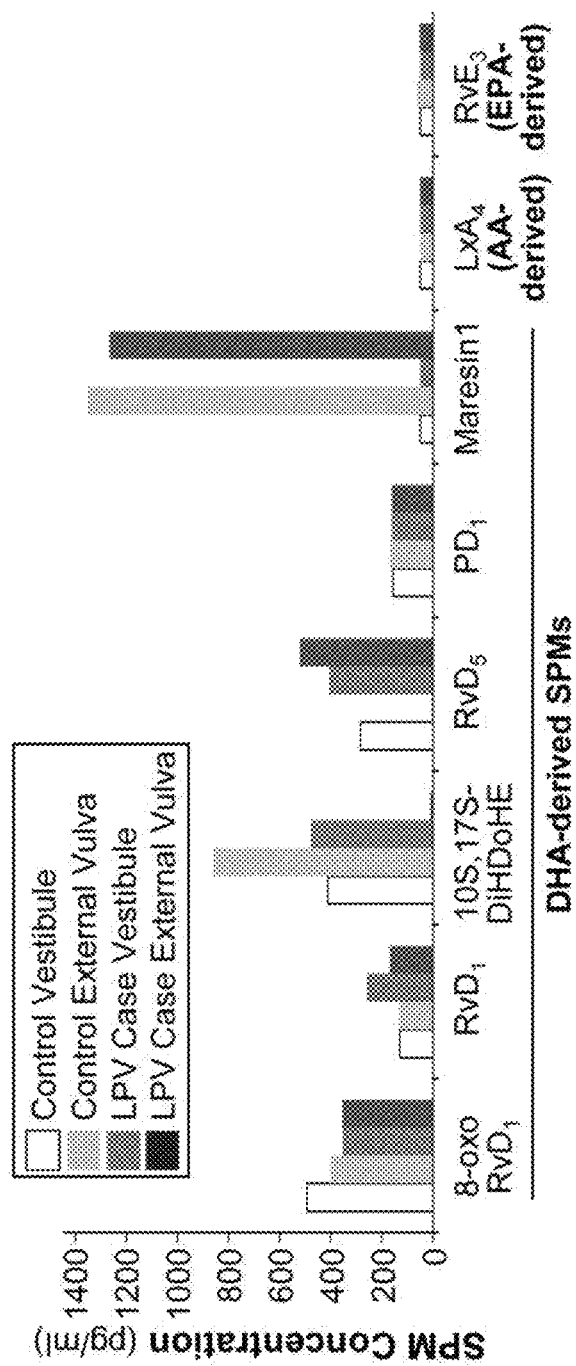
FIG. 9 is a diagram showing compounds that are produced by vulvar fibroblasts. Fibroblasts were cultured for 48 h with IL-1β (10 pg/ml), then culture media were collected and frozen immediately on dry ice under argon gas for targeted lipidomic analysis. The predominating compounds detected were derived from DHA.

Using this approach, inventors confirmed that one could induce vulvar allodynia, measure pain responses via mechanical threshold determination, and assess treatment responses. However, inventors implemented several modifications to improve the robustness of the model including the following: 1) use a genetically tractable inbred strain; 2) validation of the use of an electronic von Frey (EvF) system; 3) assessment of the impact of behavioral conditioning on pain response; 4) weekly collection of vulvovaginal lavages for pro-inflammatory mediator quantification; and 5) testing the ability of a selected compound of Formula (I) (e.g., Maresin 1) to modulate pain and inflammation in our new model. These improvements overcome two significant drawbacks in the original model: 1) MvF determinations of threshold are time-consuming and only one quantitative value is generated per test; and 2) the use of an outbred strain prevents genetic manipulation and increases study variability (original model strain is outbred CD-1). Thus, inventors elected to test two commonly used, genetically tractable mouse strains: C57BL/6 and BALB/c. Inventors had the greatest success in the C57BL/6 background and test key compounds identified in Example 2 in C57BL/6 mice (e.g., Maresin 1) as potential pain/inflammation resolving agents. Using the same experimental setup as pilot studies (FIG. 6C), but replacing MvF measurement with a Mousemet EvF system (Topcat Metrology) and implementing the other aforementioned modifications, it was found that weekly pain tests generated consistent reproducible values (average of 5 trials/mouse) for each C57BL/6 mouse (FIG. 7). Collectively, inventors saw a progressive lowering of pain thresholds in mice receiving Zymosan, which was accompanied by an increase in vaginal $PGE_2$ (FIG. 7). It was confirmed that allodynia persisted for a period of at least 5 weeks after allodynia induction (FIG. 7) before initiating daily treatments with 1 μg/mouse/day Maresin 1 for a period of 4 weeks. With treatment, inventors saw a complete restoration to the pre-induction thresholds, while $PGE_2$ levels were suppressed and maintained at levels below baseline (FIG. 8). These impressive results suggest that compounds of Formula (I) are effective.

REFERENCES

1. Sadownik, L A. Etiology, diagnosis, and clinical management of vulvodynia. *Int J Womens Health* 2014, vol. 6, pp. 437-49, PMID: 24833921, PMCID: PMC4014358.
2. Haefner, H K; Collins, M E; Davis, G D; Edwards, L; Foster, D C; Hartmann, E D; Kaufman, R H; Lynch, P J; Margesson, L J; Moyal-Barracco, M; Piper, C K; Reed, B D; Stewart, E G; Wilkinson, E J. The vulvodynia guideline. *Journal of Lower Genital Tract Disease* 2005, vol. 9, pp. 40-51, PMID: 15870521, PMCID:
3. Falsetta, M L; Foster, D C; Woeller, C F; Pollock, S J; Bonham, A D; Haidaris, C G; Stodgell, C J; Phipps, R P. Identification of novel mechanisms involved in generating localized vulvodynia pain. *Am J Obstet Gynecol* 2015, vol. 213, pp. 38 e1-12, PMID: 25683963, PMCID: PMC4485605.
4. Foster, D C; Falsetta, M L; Woeller, C F; Pollock, S J; Song, K; Bonham, A; Haidaris, C G; Stodgell, C J; Messing, S P; Iadarola, M; Phipps, R P. Site-specific mesenchymal control of inflammatory pain to yeast challenge in vulvodynia-afflicted and pain-free women. *Pain* 2015, vol. 156, pp. 386-96, PMID: 25679469, PMCID: PMC4378529.

5. Buckley, C D; Gilroy, D W; Serhan, C N; Stockinger, B; Tak, P P. The resolution of inflammation. *Nat Rev Immunol* 2013, vol. 13, pp. 59-66, PMID: 23197111, PMCID:
6. Serhan, C N; Chiang, N; Dalli, J. The resolution code of acute inflammation: Novel pro-resolving lipid mediators in resolution. *Semin Immunol* 2015, vol. 27, pp. 200-15, PMID: 25857211, PMCID: PMC4515371.
7. Serhan, C N; Chiang, N; Dalli, J; Levy, B D. Lipid mediators in the resolution of inflammation. *Cold Spring Harb Perspect Biol* 2015, vol. 7, p a016311, PMID: 25359497, PMCID:
8. Harlow, B L; Kunitz, C G; Nguyen, R H; Rydell, S A; Turner, R M; MacLehose, R F. Prevalence of symptoms consistent with a diagnosis of vulvodynia: population-based estimates from 2 geographic regions. *Am J Obstet Gynecol* 2014, vol. 210, pp. 40 e1-8, PMID: 24080300, PMCID: PMC3885163.
9. Cui, J G; Holmin, S; Mathiesen, T; Meyerson, B A; Linderoth, B. Possible role of inflammatory mediators in tactile hypersensitivity in rat models of mononeuropathy. *Pain* 2000, vol. 88, pp. 239-48, PMID: 11068111, PMCID:
10. Lin, C R; Amaya, F; Barrett, L; Wang, H; Takada, J; Samad, T A; Woolf, C J. Prostaglandin E2 receptor EP4 contributes to inflammatory pain hypersensitivity. *Journal of Pharmacology and Experimental Therapeutics* 2006, vol. 319, pp. 1096-103, PMID: 16966471, PMCID:
11. Akopians, A L; Rapkin, A J. Vulvodynia: The Role of Inflammation in the Etiology of Localized Provoked Pain of the Vulvar Vestibule (Vestibulodynia). *Semin Reprod Med* 2015, vol. 33, pp. 239-45, PMID: 26132928, PMCID:
12. Baker, D A; Peresleni, T; Kocis, C. Inflammatory Markers in Vestibulodynia [4]. *Obstet Gynecol* 2016, vol. 127 Suppl 1, pp. 1S-2S, PMID: 27176158, PMCID:
13. Falsetta, M L; Foster, D C; Woeller, C F; Pollock, S J; Bonham, A D; Haidaris, C G; Phipps, R P. A role for bradykinin signaling in chronic vulvar pain. *J Pain* 2016, PMID: 27544818, PMCID:
14. Leclair, N; Thormer, G; Sorge, I; Ritter, L; Schuster, V; Hirsch, F W. Whole-Body Diffusion-Weighted Imaging in Chronic Recurrent Multifocal Osteomyelitis in Children. *PLoS One* 2016, vol. 11, p e0147523, PMID: 26799970, PMCID: PMC4723072.
15. Foster, D C; Piekarz, K H; Murant, T I; LaPoint, R; Haidaris, C G; Phipps, R P. Enhanced synthesis of proinflammatory cytokines by vulvar vestibular fibroblasts: implications for vulvar vestibulitis. *Am J Obstet Gynecol* 2007, vol. 196, pp. 346 e1-8, PMID: 17403416, PMCID:
16. Morgan, T K; Allen-Brady, K L; Monson, M A; Leclair, C M; Sharp, H T; Cannon-Albright, L A. Familiality analysis of provoked vestibulodynia treated by vestibulectomy supports genetic predisposition. *Am J Obstet Gynecol* 2016, vol. 214, pp. 609 e1-7, PMID: 26627726, PMCID:
17. Tommola, P; Butzow, R; Unkila-Kallio, L; Paavonen, J; Meri, S. Activation of vestibule-associated lymphoid tissue in localized provoked vulvodynia. *Am J Obstet Gynecol* 2015, vol. 212, pp. 476 e1-8, PMID: 25448516, PMCID:
18. Tommola, P; Unkila-Kallio, L; Paetau, A; Meri, S; Kalso, E; Paavonen, J. Immune activation enhances epithelial nerve growth in provoked vestibulodynia. *Am J Obstet Gynecol* 2016, PMID: 27457118, PMCID:
19. Cassone, A. Vulvovaginal *Candida albicans* infections: pathogenesis, immunity and vaccine prospects. *BJOG* 2015, vol. 122, pp. 785-94, PMID: 25052208, PMCID:
20. Davies, S; Johnson, E; White, D. How to treat persistent vaginal yeast infection due to species other than *Candida albicans*. *Sex Transm Infect* 2013, vol. 89, pp. 165-6, PMID: 23180861, PMCID:
21. Giraldo, P; von Nowaskonski, A; Gomes, F A; Linhares, I; Neves, N A; Witkin, S S. Vaginal colonization by *Candida* in asymptomatic women with and without a history of recurrent vulvovaginal candidiasis. *Obstet Gynecol* 2000, vol. 95, pp. 413-6, PMID: 10711554, PMCID:
22. Harriott, M M; Lilly, E A; Rodriguez, T E; Fidel, P L, Jr.; Noverr, M C. *Candida albicans* forms biofilms on the vaginal mucosa. *Microbiology* 2010, vol. 156, pp. 3635-44, PMID: 20705667, PMCID: 3068702.
23. Donders, G; Bellen, G. Characteristics of the pain observed in the focal vulvodynia syndrome (VVS). *Med Hypotheses* 2012, vol. 78, pp. 11-4, PMID: 22041052, PMCID:
24. Farmer, M A; Taylor, A M; Bailey, A L; Tuttle, A H; MacIntyre, L C; Milagrosa, Z E; Crissman, H P; Bennett, G J; Ribeiro-da-Silva, A; Binik, Y M; Mogil, J S. Repeated vulvovaginal fungal infections cause persistent pain in a mouse model of vulvodynia. *Sci Transl Med* 2011, vol. 3, p 101ra91, PMID: 21937756, PMCID: PMC3243907.
25. Bergeron, S; Binik, Y M; Khalife, S; Pagidas, K; Glazer, H I. Vulvar vestibulitis syndrome: reliability of diagnosis and evaluation of current diagnostic criteria. *Obstet Gynecol* 2001, vol. 98, pp. 45-51, PMID: 11430955, PMCID:
26. Edwards, R R; Doleys, D M; Fillingim, R B; Lowery, D. Ethnic differences in pain tolerance: clinical implications in a chronic pain population. *Psychosom Med* 2001, vol. 63, pp. 316-23, PMID: 11292281, PMCID:
27. Wolf, J; Weinberger, B; Arnold, C R; Maier, A B; Westendorp, R G; Grubeck-Loebenstein, B. The effect of chronological age on the inflammatory response of human fibroblasts. *Exp Gerontol* 2012, vol. 47, pp. 749-53, PMID: 22790019, PMCID: PMC3427851.
28. Brown, C S; Foster, D C; Wan, J Y; Rawlinson, L A; Bachmann, G A; Gabapentin Study, G. Rationale and design of a multicenter randomized clinical trial of extended release gabapentin in provoked vestibulodynia and biological correlates of response. *Contemp Clin Trials* 2013, vol. 36, pp. 154-65, PMID: 23816491, PMCID: PMC3779071.
29. Foster, D C; Kotok, M B; Huang, L S; Watts, A; Oakes, D; Howard, F M; Poleshuck, E L; Stodgell, C J; Dworkin, R H. Oral desipramine and topical lidocaine for vulvodynia: a randomized controlled trial. *Obstetrics and Gynecology* 2010, vol. 116, pp. 583-93, PMID: 20733439, PMCID:
30. Chaplan, S R; Bach, F W; Pogrel, J W; Chung, J M; Yaksh, T L. Quantitative assessment of tactile allodynia in the rat paw. *J Neurosci Methods* 1994, vol. 53, pp. 55-63, PMID: 7990513, PMCID:
31. Baglole, C J; Maggirwar, S B; Gasiewicz, T A; Thatcher, T H; Phipps, R P; Sime, P J. The aryl hydrocarbon receptor attenuates tobacco smoke-induced cyclooxygenase-2 and prostaglandin production in lung fibroblasts through regulation of the NF-kappaB family member RelB. *J Biol Chem* 2008, vol. 283, pp. 28944-57, PMID: 18697742, PMCID: 2570856
32. Colucci, M; Maione, F; Bonito, M C; Piscopo, A; Di Giannuario, A; Pieretti, S. New insights of dimethyl sulphoxide effects (DMSO) on experimental in vivo models of nociception and inflammation. *Pharmacol Res* 2008, vol. 57, pp. 419-25, PMID: 18508278, PMCID:

33. Galer, B S. A comparative subjective assessment study of PENNSAID(R) and Voltaren Gel(R), two topical formulations of diclofenac sodium. *Pain Pract* 2011, vol. 11, pp. 252-60, PMID: 20854305, PMCID:
34. Xie, Y; Shi, L; Xiong, X; Wu, E; Veasley, C; Dade, C. Economic burden and quality of life of vulvodynia in the United States. *Curr Med Res Opin* 2012, vol. 28, pp. 601-8, PMID: 22356119, PMCID:

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A method of reducing, preventing, or treating vulvodynia in a subject, comprising administering to a subject in need an effective amount of a compound having the Formula (I):

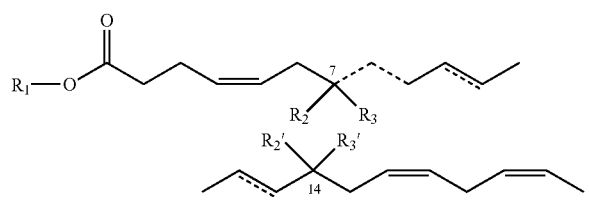

wherein ==== is a double bond with the Z or E configuration;
wherein

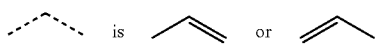

with the Z or E configuration; wherein the carbon at C7 and C14 are, independently, either R or S;
wherein $R_1$, is selected from hydrogen, (C1-C6) alkyl, glyceryl, (C3-C8) cycloalkyl, cyclohexyl, (C4-C11) cycloalkylalkyl, (C5-C15) aryl, (C6-C16) arylalkyl, 2-6 membered heteroalkyl, 3-8 membered cycloheteroalkyl, 4-11 membered cycloheteroalkylalkyl, (C5-C14) heteroaryl and 6-21 membered heteroarylalkyl;
wherein each of $R_2$ and $R_{2'}$ is independently a hydroxyl group or a hydrogen atom, with the proviso that at least one of $R_2$ and $R_{2'}$ is a hydroxyl group;
wherein $R_3$, if present, is selected from hydrogen, (C1-C6) alkyl, (C3-C8) cycloalkyl, cyclohexyl, (C4-C11) cycloalkylalkyl, (C5-C15) aryl, (C6-C16) arylalkyl, and 2-6 membered heteroalkyl;
wherein $R_{3'}$ is selected from hydrogen, (C1-C6) alkyl, (C3-C8) cycloalkyl, (C4-C11) cycloalkylalkyl, (C5-C15) aryl, (C6-C16) arylalkyl, and 2-6 membered heteroalkyl;
or a pharmaceutically acceptable salt thereof.

2. The method of claim 1, wherein compounds of Formula (I) are in the triglyceride, diglyceride and/or monoglyceride form.

3. The method of claim 1, wherein $R_1$ is methyl or ethyl.

4. The method of claim 1, wherein the compound of Formula (I) is selected from: Maresin 1, 7S-Maresin 1, 14S-methyl-Maresin 1, 14R-methyl-Maresin 1, 14R/S-methyl-Maresin 1, 7R,14S-dihydroxi-7,14-dimethyl-docosa-4Z,8E,10E,12Z,16Z,19Z-hexaenoic acid, 7R-methyl-Maresin 1, 7S-methyl-Maresin 1, 7S,14S-diHDHA, 14S-HDHA, 14R-HDHA, 14R-methyl-HDHA, 14S-methyl-HDHA or a pharmaceutically acceptable salt or ester thereof.

5. The method of claim 1, wherein the compound of Formula (I) is selected from: 14S-methyl-Maresin 1, 14R-methyl-Maresin 1, 14R/S-methyl-Maresin 1, 7R,14S-dihydroxi-7,14-dimethyl-docosa-4Z,8E,10E,12Z,16Z,19Z-hexaenoic acid, or a pharmaceutically acceptable salt or ester thereof.

6. The method of claim 1, wherein the compound of Formula (I) is selected from: 14S-HDHA, 14R-HDHA, 14S/R-HDHA, and a pharmaceutically acceptable salt or ester thereof.

7. The method of claim 1, wherein the vulvodynia is localized provoked vulvodynia.

8. The method of claim 1, wherein the compound of Formula (I) is administered at 0.0001 mg/kg-100 mg/kg.

9. The method of claim 1, wherein the compound of Formula (I) is administered once a week, 2-3 times a week, once a day, twice a day, or three times a day.

10. The method of claim 1, wherein the compound of Formula (I) is administered before the subject is exposed to a secondary pain-causing stimulation.

11. The method of claim 1, wherein the treatment site comprises the vulvar vestibule.

12. The method of claim 1, wherein the at least one compound of Formula (I) is administered with at least one additional therapeutic agent, said at least one additional therapeutic agent is one or more specialized pro-resolving mediators (SPMs) or one or more SPM precursors not included in Formula (I), an anti-microbial agent, or an antiviral agent.

13. The method of claim 1, wherein the at least one compound of Formula (I) is administered with at least one additional therapeutic agent, said at least one additional therapeutic agent is one or more specialized pro-resolving mediators (SPMs) or one or more SPM precursors not included in Formula (I).

14. The method of claim 12, wherein the SPMs or SPM precursors not included in Formula (I) are 17-HDHA and 18-HEPE; or a pharmaceutically acceptable salt or ester thereof.

15. The method of claim 1, wherein compound of Formula (I) or a composition thereof is topical administered.

* * * * *